US011404143B2

United States Patent
Alberti et al.

(10) Patent No.: US 11,404,143 B2
(45) Date of Patent: Aug. 2, 2022

(54) METHOD AND SYSTEMS FOR THE INDEXING OF BIOINFORMATICS DATA

(71) Applicant: GenomSys SA, Lausanne (CH)

(72) Inventors: Claudio Alberti, Geneva (CH); Giorgio Zoia, Lausanne (CH); Daniele Renzi, Lausanne (CH); Mohamed Khoso Baluch, Chantilly, VA (US)

(73) Assignee: GenomSys SA, Lausanne (CH)

( * ) Notice: Subject to any disclaimer, the term of this patent is extended or adjusted under 35 U.S.C. 154(b) by 263 days.

(21) Appl. No.: 16/337,642

(22) PCT Filed: Jul. 11, 2017

(86) PCT No.: PCT/US2017/041585
§ 371 (c)(1),
(2) Date: Mar. 28, 2019

(87) PCT Pub. No.: WO2018/071079
PCT Pub. Date: Apr. 19, 2018

(65) Prior Publication Data
US 2020/0035328 A1    Jan. 30, 2020

(30) Foreign Application Priority Data

Oct. 11, 2016  (WO) ............... PCT/EP2016/074297
Oct. 11, 2016  (WO) ............... PCT/EP2016/074301
(Continued)

(51) Int. Cl.
*G16B 30/10*    (2019.01)
*G16B 30/00*    (2019.01)
(Continued)

(52) U.S. Cl.
CPC ............ *G16B 30/10* (2019.02); *G06F 3/048* (2013.01); *G06F 7/00* (2013.01); *G06F 16/2282* (2019.01);
(Continued)

(58) Field of Classification Search
CPC ........ G16B 30/10; G16B 30/00; G16B 30/20; G16B 40/00; G16B 40/10; G16B 99/00;
(Continued)

(56) References Cited

U.S. PATENT DOCUMENTS 6,303,297 B1    10/2001    Lincoln et al.
6,865,168 B1    3/2005    Sekine
(Continued)

FOREIGN PATENT DOCUMENTS

WO    2008/100206 A1    8/2008
WO    2014/145503 A2    9/2014
(Continued)

OTHER PUBLICATIONS

McKenna, Aaron, et al., "The Genome Analysis Toolkit: A MapReduce framework for analyzing next-generation DNA sequencing data", Genome Research, vol. 20, © 2010 by Cold Spring Harbor Laboratory, 8 pages.*
(Continued)

*Primary Examiner* — Robert Stevens
(74) *Attorney, Agent, or Firm* — Howard & Howard Attorneys PLLC

(57) ABSTRACT

Method and apparatus for the indexing of genome sequence data produced by genome sequencing machines. The proposed method can be applied both to raw sequence data produced by sequencing machines and to those sequence reads that cannot be mapped on any reference sequence according to specific matching criteria. This invention describes a method to partition and index unaligned
(Continued)

sequence reads to enable browsing and efficient selective access.

21 Claims, 15 Drawing Sheets

(30) Foreign Application Priority Data

| Oct. 11, 2016 | (WO) | PCT/EP2016/074307 |
|---|---|---|
| Oct. 11, 2016 | (WO) | PCT/EP2016/074311 |
| Feb. 14, 2017 | (WO) | PCT/US2017/01781 |
| Feb. 14, 2017 | (WO) | PCT/US2017/017842 |

(51) Int. Cl.

| G16B 40/00 | (2019.01) |
|---|---|
| G06F 16/23 | (2019.01) |
| H03M 7/30 | (2006.01) |
| G06F 16/28 | (2019.01) |
| G06F 16/22 | (2019.01) |
| G16B 20/20 | (2019.01) |
| G06F 21/60 | (2013.01) |
| G06F 3/048 | (2013.01) |
| G16B 99/00 | (2019.01) |
| G06F 7/00 | (2006.01) |
| G16B 50/50 | (2019.01) |
| G16B 30/20 | (2019.01) |
| G16B 50/30 | (2019.01) |
| G16B 50/40 | (2019.01) |
| G06F 21/62 | (2013.01) |
| G16B 45/00 | (2019.01) |
| G16B 50/10 | (2019.01) |
| G16B 40/10 | (2019.01) |
| G16B 20/10 | (2019.01) |

(52) U.S. Cl.
CPC ........ *G06F 16/2365* (2019.01); *G06F 16/285* (2019.01); *G06F 21/602* (2013.01); *G06F 21/6218* (2013.01); *G16B 20/10* (2019.02); *G16B 20/20* (2019.02); *G16B 30/00* (2019.02); *G16B 30/20* (2019.02); *G16B 40/00* (2019.02); *G16B 40/10* (2019.02); *G16B 45/00* (2019.02); *G16B 50/10* (2019.02); *G16B 50/30* (2019.02); *G16B 50/40* (2019.02); *G16B 50/50* (2019.02); *G16B 99/00* (2019.02); *H03M 7/3086* (2013.01); *H03M 7/70* (2013.01)

(58) Field of Classification Search
CPC ........ G16B 50/50; G16B 50/30; G16B 50/40; G16B 50/10; G16B 20/20; G16B 20/10; G16B 45/00; G06F 16/2365; G06F 16/285; G06F 16/2282; G06F 7/00; G06F 21/602; G06F 21/6218; G06F 3/048; H03M 7/70; H03M 7/3086
USPC .................................................... 707/693
See application file for complete search history.

(56) References Cited

U.S. PATENT DOCUMENTS

| 2004/0023231 A1 | 2/2004 | Abu-Khabar et al. |
|---|---|---|
| 2004/0153255 A1 | 8/2004 | Ahn |
| 2005/0187916 A1 | 8/2005 | Levin et al. |
| 2008/0077607 A1 | 3/2008 | Gatawood et al. |
| 2012/0059670 A1 | 3/2012 | Sanborn et al. |
| 2012/0170595 A1* | 7/2012 | Lee .................... H04N 21/4341 370/470 |
| 2012/0179712 A1* | 7/2012 | Bestgen ............. G06F 16/2237 707/769 |
| 2012/0230338 A1* | 9/2012 | Ganeshalingam ..... G16B 30/00 370/392 |
| 2013/0204851 A1 | 8/2013 | Bhola et al. |
| 2013/0332133 A1 | 12/2013 | Horn et al. |
| 2014/0228223 A1* | 8/2014 | Gnirke ............... C12N 15/1031 506/2 |
| 2014/0371109 A1 | 12/2014 | McMillen et al. |
| 2014/0379270 A1 | 12/2014 | Park |
| 2015/0032711 A1 | 1/2015 | Kunin |
| 2015/0227686 A1 | 8/2015 | Sheinin et al. |
| 2015/0234870 A1* | 8/2015 | Kumar .................... G06F 16/13 707/807 |
| 2015/0286495 A1 | 10/2015 | Lee |
| 2015/0379195 A1* | 12/2015 | Wang ..................... G16B 30/00 506/4 |
| 2016/0191076 A1 | 6/2016 | Leighton et al. |

FOREIGN PATENT DOCUMENTS

| WO | 2015/197201 A1 | 12/2015 | |
|---|---|---|---|
| WO | WO 2015/197201 A1 * | 12/2015 | ............. H03M 7/30 |

OTHER PUBLICATIONS

"Compression of genomic sequencing data", Wikipedia, downloaded from https://en.wikipedia.org/wiki/Compression_of_genomic_sequencing_data on Aug. 18, 2021, pp. 1-3.*
Brandon, Marty C., et al., "Data structures and compression algorithms for genomic sequence data", Bioinformatics, vol. 25, No. 14, ©2009, Oxford University Press, pp. 1731-1738.*
Massie, Matt, et al., "ADAM: Genomics Formats and Processing Patterns for Cloud Scale Computing", Electrical Engineering and Computer Sciences, Univ. of California at Berkeley, Technical Report No. UCB/EECS-20130207, http://www.eecs.berkeley.edu/Pubs/TechRpts/2013/EECS-2013-207.html, Dec. 15, 2013, 24 pages.*
Zhu, Zexuan, et al., "High-throughput DNA sequence data compression", Briefings in Bioinformatics, vol. 16, Issue 1, Jan. 2015, pp. 1-15.*
Numanagic et al., Comparison of High-Throughput Sequencing Data Compression Tools, Nature Methods, Oct. 24, 2016, vol. 13, pp. 1005-1008 (downloaded from the internet Jun. 11, 2019) 5 pages.
International Search Report (PCT/US2017/041585); dated Oct. 17, 2017 2 pages.
Written Opinion (PCT/US2017/041585); dated Oct. 17, 2017 17 pages.
International Preliminary Report on Patentability (PCT/US2017/041585); dated Jan. 24, 2019 5 pages.
Yanovsky, Vladimir, ReCoil—an algorithm for compression of extremely large datasets of DNA data, Algorimths for Molecular Biology, Biomed Central LTD. LO., vol. 6, No. 1., Oct. 11, 2011, 9 pages.
Namiki, Youhei et al., Acceleration of sequence clustering using longest common subsequence filtering, BMC Bioinformatics, Biomed Central, London, GB, vol. 14, No. Suppl 8, May 9, 2013, 8 pages.
Panneel, Jens, Implementation and optimization of CABAC in a genomic data compression framework with support for random access, dissertatieFaculty of Engineering and Architecture, Jan. 1, 2015, 81 pages.
Anonymous: CRAM format specification (Ver 3.0), Sep. 8, 2016, the master version of this document can be found at https://github.com/samtools/hts-specs, 26 pages.
Anonymous: "SAM", Mar. 11, 2015, URL:https://web.archive.org/web/20150311045750/http://davetang.org/wiki/tiki-index.pph?page=SAM, 5 pages.
Supplementary European Search Report, Application No. EP 17 86 0980, dated May 29, 2020 12 Pages.
Ochoa, I et al., "Aligned genomic data compression via improved modelling"; J Bioinform Comput Biol. NIH Public Access; 2014,12:1442002, (Also accessible online at: https://www.ncbi.nlm.nih.gov/pmc/articles/PMC566 6573/) 18 Pages.

(56) References Cited

OTHER PUBLICATIONS

CRAM format specification (Ver 2.1), cram—dev@ebi.ac.uk Mar. 14, 2014, the master version of this document can be found at https://github.com/samtools/hts-specs 23 pages.

Li H. Durbin R., "Fast and accurate short read alignment with Burrows-Wheeler transform", Bioinformatics, Mar. 8, 2013, pp. 1-8, http://bio- bwa.sourceforge.net/bwa.shtml.

Utilities for the Sequence Alignment/Map (SAM) format, Dec. 15, 2015, http://www.htslib.org/doc/samtools-I.3.html 22 pages.

Hsi-Yang, Fritz M, et al., "Efficient storage of high throughput DNA sequencing data using reference-based compression", article published on-line before print, article, supplemental material, and publication date are at :http://www.genome.org/cgi/doi/10.1101/gr. 114819.110, freely available online through the Genome Research Open Access option Feb. 10, 2020 8 pages.

Mohamed, Nabeel M. et al., "Accelerating Data-Intensive Genome Analysis in the Cloud", Mar. 2013, 5th International Conference on Bioinformatics and Computational Biology (BICoB) 8 pages.

Sequence Alignment/Map Format Specification, The SAM/BAM Format Specification Working Group, Sep. 12, 2014, the master version of this document can be found at https://github.com/samtools/hts-specs 17 pages.

Hach, Faraz et al., DeeZ: reference-based compression by local assembly, Nature Methods, Nov. 2014, pp. 1082-1084, vol. 11, No. 11.

Li, Heng et al., The Sequence Alignment/Map Format and SAMtools, Bioinformatics, Jun. 8, 2009, pp. 2078-2079, vol. 25, No. 16.

CRAM format specification (Ver 3.0), Jun. 1, 2015, the master version of this document can be found at https://github.com/samtools/hts-specs 26 pages.

Barnett, Derek W. et al., BamTools: a C++ API and toolkit for analyzing and managing BAM files, Bioinformatics, Apr. 14, 2011, vol. 27, No. 12 p. 1691.

Multiplexing, downloaded on Feb. 7, 2020 from https://en.wikipedia.org/w/index.php?title=multiplexing&oldid=739917170, 9 pages.

Npg_ranger project, Sep. 2016, https://github.com/wtsi-npg/npg_ranger, 2 pages.

Information Sciences Institute, Internet Protocol, Sep. 1981, pp. 1-97, https://tools.ietf.org/html/rfc791, , University of Southern California, Marina del Rey, California.

Layer, Ryan M., Getting samtools/bcftools to work with S3, Apr. 2, 2016, 3 pages, https://ryanmlayer.wordpress.com/2016/04/27/getting-samtoolsbcftools-to-work-with-s3/ 3 pages.

Htslib library version 1.3, Sep. 1981, 2 pages, https://github.com/samtools/htslib/releases/tag/1.3.

Tang, Dave, download on Feb. 7, 2020 from https://web.archive.org/web/20150311045750/http://davetang.org/wiki/tiki-index.php?page=SAM, 5 pages.

Alberti, Claudio, Core Experiment 1 on Genome Compression summary, International Organisation for Standardisation, Jan. 2017, 6 pages, Geneva, CH.

PacBio Alignment File Format (cmp.h5) Specification, 2015, pp. 1-14, https://pacbiofileformats.readthedocs.io/en/3.0/legacy/CmpH5Spec.html.

Ruiqiang, Li et al., "De novo assembly of human genomes with massively parallel short read sequencing", Genome Res., Feb. 20, 2010, pp. 265-272, 20(s), Cold Spring Harbor Laboratory Press 19 pages.

Jones, Daniel C. et al., "Compression of next-generation sequencing reads aided by highly efficient de novo assembly", Nucleic Acids Research, Dec. 2012, 17 pages, 40(22), Oxford University Press.

Kozanitis, Christos et al., "Compressing Genomic Sequence Fragments Using SlimGene", Journal of Computational Biology, Mar. 2011, 18(3), Mary Ann Liebert, Inc. 18 pages.

Hach, Faraz et al., "SCALCE: boosting sequence compression algorithms using locally consistent encoding", Bioinformatics. Dec. 1, 2012 pp. 3051-3057, 28(23), Oxford University Press.

\* cited by examiner

Figure 2

|  | Sequence 1 | | | Sequence 2 | | | ... | Sequence j | |
|---|---|---|---|---|---|---|---|---|---|
|  | 1 | ... | N1 | 1 | ... | N2 | ... | 1 | Nj |
| Class P | Ps11, Pe11, Op11 | ... | Ps1N1, Pe1N1, Op1N1 | Ps21, Pe21, Op21 | ... | Ps2N2, Pe2N2, Op2N2 | ... | PsJ1, PeJ1, OpJ1 | PsJNj, PeJNj, OpjNj |
| Class N | Ns11, Ne11, On11 | ... | Ns1N1, Ne1N1, On1N1 | Ns21, Ne21, On21 | ... | Ns2N2, Ne2N2, On2N2 | ... | NsJ1, NeJ1, OnJ1 | NsJNj, NeJNj, OnjNj |
| Class M | Ms11, Me11, Om11 | ... | Ms1N1, Me1N1, Om1N1 | Ms21, Me21, Om21 | ... | Ms2N1, Me2N1, Om2N2 | ... | MsJ1, MeJ1, OmJ1 | MsJNj, MeJNj, OmjNj |
| Class I | Is11, Ie11, Oi11 | ... | Is1N1, Ie1N1, Oi1N1 | Is21, Ie21, Oi21 | ... | Is2N2, Ie2N2, Oi2N2 | ... | IsJ1, IeJ1, OiJ1 | IsJNj, IeJNj, OiJNj |
| Class HM | HMs11, HMe11, Ohm11 | | HMs1N1, HMe1N1, Ohm1N1 | HMs21, HMe21, Ohm21 | | HMs2N2, HMe2N2, Ohm2N2 | | HMsJ1, HMeJ1, OhmJ1 | HMsJNj, HMeJNj, OhmJNj |
| Class U | $S_1$ $P_1$ | | $S_2$ $P_2$ | | | $S_K$ $P_K$ | | | $S_M$ $P_M$ |

$S_i$ = encoded signature associated to the $i^{th}$ cluster. It is composed by one or more unsigned N-bits integers
$P_i$ = vectors of pointers to the first byte on the storage medium of the encoded descriptors streams contained by each Access Unit containing the reads associated to the $i^{th}$ signature

Figure 7

| Cluster_ID | U_Cluster[Cluster_ID][0] | U_Cluster[Cluster_ID][1] | Binary representation | Signature |
|---|---|---|---|---|
| 0 | 5897 | $P_0$ | (16X0)00010111000011001 | ACCTAAGC |
| 1 | 64299 | $P_1$ | (16X0)11110110010101011 | TTGTAGGT |
| ... | ... | ... | ... | ... | zero padding

Alphabet = {A, C, G, T}

| Alphabet binarization | |
|---|---|
| Symbol | Binary representation |
| A | 00 |
| C | 01 |
| G | 10 |
| T | 11 |
| M | $\log_2 4 = 2$ |

U_signature_size = N = 32
U_signature_length = $S_L$ = 8
$\log_2$(alphabet size) = M = 2
M × $S_L$ = 16 < 32

$P_i$ = pointer to the first byte of the storage medium of the Access Unit encoding the reads associated to the i$^{th}$ signature

Figure 8

| Cluster_ID | U_Cluster[Cluster_ID][0] | U_Cluster[Cluster_ID][1] | Binary representation | Signature |
|---|---|---|---|---|
| 0 | 0 | $P_0$ | (1 3X 0)(000) | - |
|  | 12 |  | 00 001100 | AT |
|  | 9 |  | 00 001001 | AA |
|  | 26 |  | 00 011010 | GC |
| 1 | 3 | $P_1$ | 00 011011 | G |
|  | 35 |  | 100(00)011 | TG |
|  | 9 |  | 00 001001 | AA |
| 2 | ... |  | ... | ... |

| Alphabet = {A, C, G, T} | |
|---|---|
| Alphabet binarization | |
| Symbol | Binary representation |
| A | 001 |
| C | 010 |
| G | 011 |
| T | 100 |
| separator | 000 |
| M | ceil(log$_2$ 4+1) = 3 |

$P_i$ = pointer to the first byte of the storage medium of the Access Unit encoding the reads associated to the $i^{th}$ signature U_signature_size = N = 8
log$_2$ (alphabet size + 1) = M = 3

Figure 9

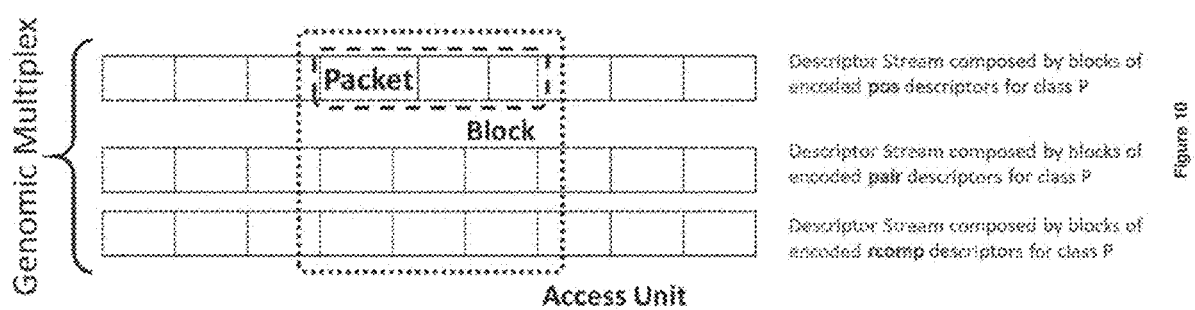

METHOD AND SYSTEMS FOR THE INDEXING OF BIOINFORMATICS DATA

CROSS-REFERENCE TO RELATED APPLICATIONS

CROSS-REFERENCE TO RELATED APPLICATIONS

The present application is the National Stage of International Patent Application No. PCT/US2017/041585, filed Jul. 11, 2017, which claims priority to and all the benefits of Patent Applications PCT/EP2016/074311, filed Oct. 11, 2016, PCT/EP2016/074301, filed Oct. 11, 2016, PCT/EP2016/074307, filed Oct. 11, 2016, PCT/EP2016/074297, filed Oct. 11, 2016, PCT/US2017/017842, filed Feb. 14, 2017, and PCT/US2017/017841, filed Feb. 14, 2017, all disclosures of which are expressly incorporated herein by reference in their entirety.

TECHNICAL FIELD

This disclosure provides a novel method of partitioning and indexing genome sequencing data so as to enable selective access and pattern matching. The disclosed indexing method reduces the required processing power and data access time when searching for specific nucleotides sequences among the unaligned sequence reads. The disclosed method can be applied to:
- raw sequence data produced by genome sequencing machines,
- unmapped reads that fail to map on any region of one or more reference sequences during a process of reads mapping according to specified matching criteria,
- unaligned reads that fail to align with any other read to form longer sequences (also known as "contigs") during a process of sequence reads assembly (also known as reference-less alignment) according to specified matching criteria.

BACKGROUND

An appropriate indexing of genome sequencing data is fundamental to enable efficient genomic analysis applications such as, for example but not as a limitation, gene discovery. Gene discovery is the process of identifying regions of an organism's genome which are related to the development of traits or phenotypes. Gene discovery requires the search of specific patterns of nucleotides in one or more genomic samples under study. Likewise, other genome analysis applications require the use of pattern matching techniques to identify configurations of nucleotides of interest. In some cases pattern matching is seen as an alternative to sequence alignment techniques whereby the sequence data are mapped on a pre-existing reference sequence in order to build longer genomic sequences. The most used genome information representations of sequencing data are based on the FASTQ format for raw reads and SAM and CRAM for aligned reads. These solutions do not support any form of indexing for raw or unmapped reads and store them as an unordered sequence of records. These implies that any search for specific patterns requires decoding and parsing the entire dataset.

The present invention aims at indexing raw or unmapped genomic sequence reads by:
- clustering reads according to a shared common subsequence. All reads belonging to a cluster contain a specific sequence of nucleotides with possibly some mismatches according to defined clustering constraints. Throughout this invention disclosure the common sequence is called cluster signature,
- encoding the cluster signature as sequence of one or more integer numbers representing the signature nucleotides,
- storing the encoded signatures in an ordered or unordered vector,
- coding the vector of encoded signatures together with the raw, unmapped or unaligned reads belonging to Class U as defined in this disclosure.

The most relevant improvements of such approach with respect to existing methods consist in:
1. the possibility to perform pattern matching on entire clusters of reads instead of single reads,
2. the possibility to perform parallel pattern matching on several clusters at the same time,
3. the possibility to order raw or unmapped reads according to criteria related to the cluster signatures characteristics,
4. the increase of gene discovery performance by enabling comparison of known genes with clusters signatures.

BRIEF DESCRIPTION OF THE DRAWINGS

FIG. 2 shows an example of four reads sharing the same signature but with different levels of accuracy. read1 contains the exact signature; read2 contains the signature with 2 mismatches; read3 contains the signature except for one base (deletion); read4 contains the signature with an extra base (insertion).

FIG. 7 shows that, when coding raw, unmapped or unaligned reads, the Master Index Table comprises two vectors containing the encoded signatures and the pointers to the corresponding blocks of encoded descriptors contained by the Access Units on the storage medium.

FIG. 8 shows an example of how to decode constant length signatures composed by 8 nucleotides and encoded as 32-bit integers.

FIG. 9 shows an example of how to decode variable length signatures composed by encoded as 8-bit integers.

FIG. 10 shows how an Access Unit contains blocks of entropy coded descriptors used to represent reads of the same genomic data class. Blocks are divided in packets for network transfer.

SUMMARY

Figure 1:
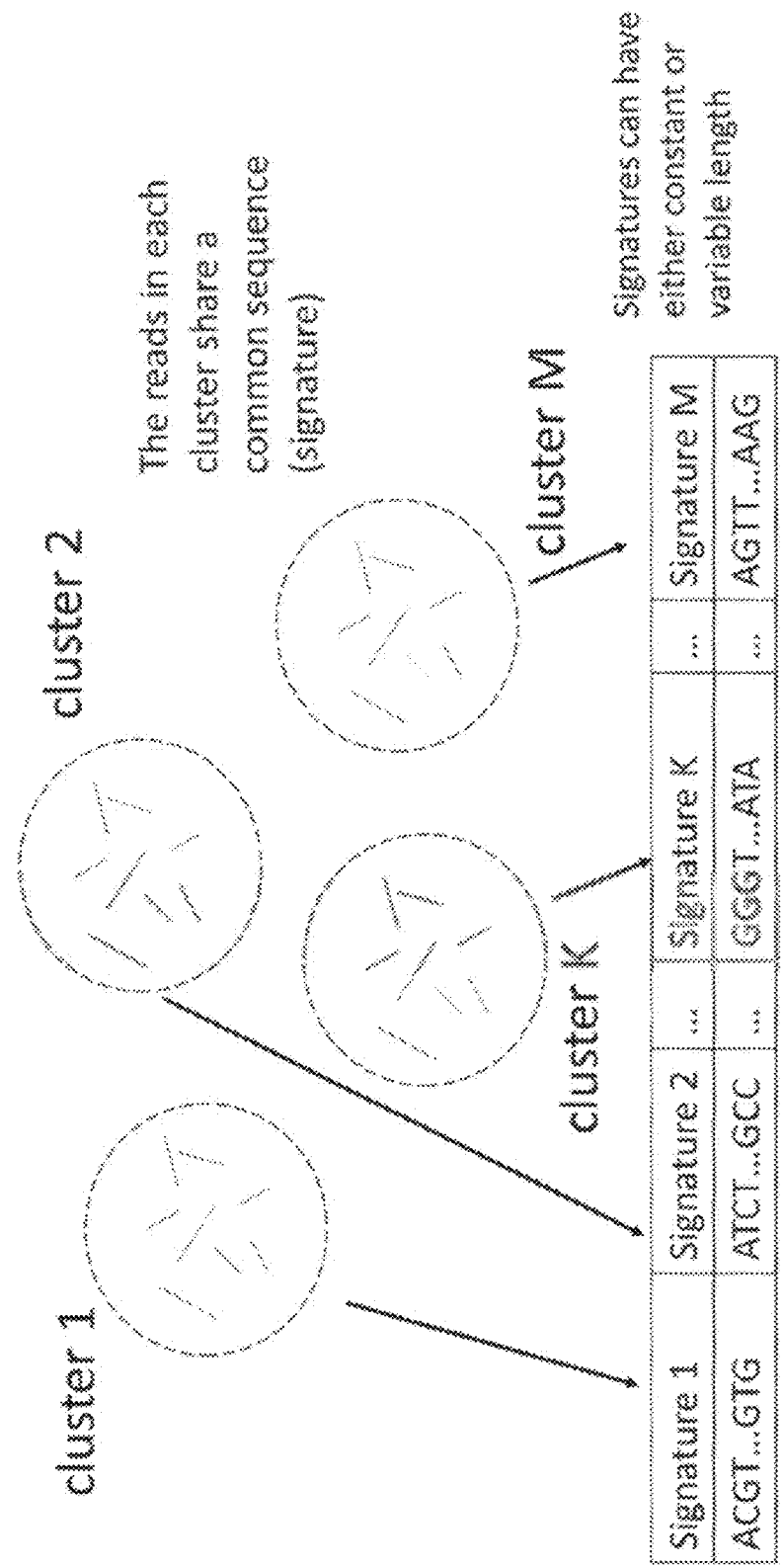
FIG. 1 shows how raw, unmapped and unaligned reads are clustered according a shared subsequence of nucleotides called "signature".

The features of the claims below solve the problem of existing prior art solutions by providing a method for encoding genome sequence data, said genome sequence data comprising reads of sequences of nucleotides, said method comprising the steps of:

partitioning said reads into clusters of reads which share a common sequence or subsequence of nucleotides called "cluster signature", encoding said clustered reads as a multiplicity of blocks of syntax elements, structuring said blocks of syntax elements with header information thereby creating successive Access Units.

In another aspect the encoding method further comprises encoding said clusters signatures by:

associating each nucleotide of the supported alphabet to a unique binary representation, concatenating the binary representations of each nucleotide in a signature to obtain a bitstring representing the encoded signature.

In another aspect the encoding method further comprises the step in which each cluster of encoded sequence reads is identified by said encoded signature.

In another aspect said blocks of syntax elements comprise a master index table, comprising cluster signatures encoded associating each nucleotide of the supported alphabet to a unique binary representation, concatenating the binary representations of each nucleotide in a signature to obtain a bitstring representing the encoded signature and is associated to a vector of integer values representing the positions on a storage medium of the blocks of encoded syntax elements representing the sequence reads belonging to each cluster.

In another aspect said blocks of syntax elements comprise a genomic dataset header comprising a dataset group identifier used to uniquely identify each dataset group, a genomic dataset identifier used to uniquely identify each dataset, a brand identifier used to identify the data format specification the dataset complies with, a minor version number used to identify the data format specification the dataset complies with, the length of encoded genomic reads in nucleotides used to signal constant length reads, a flag signaling the presence of paired end reads, a flag signaling the presence of blocks headers, a flag signaling the order in which Access Units are stored on a storage medium, the number of reference sequences used to code the dataset, a numeric identifier per each reference sequence used to uniquely identify each reference sequence, a string identifier per each reference sequence used to uniquely identify each reference sequence, the number of coded Access Units per reference sequence used to count the Access Units associated to each reference sequence, the type of coded genomic data used to distinguish among aligned reads, unaligned reads, unmapped reads and reference sequences, the number of data classes coded in the dataset, the number of descriptors used per each data class coded in the dataset used during the decoding process, the total number of clusters used to index encoded unmapped reads, the number of bits used to represent the integer values used to encode the cluster signatures used to decode encoded clusters signatures, a flag signaling if all the cluster signatures have the same length in terms of number of nucleotides the length of the clusters signatures.

In another aspect of said encoding method said genomic reads are paired

In another aspect of said encoding method said genomic data are entropy coded

A method for decoding encoded genomic data comprising the steps of:

parsing Access Units containing said encoded genomic data to extract multiple blocks of syntax elements by employing header information, decoding said multiplicity of blocks of syntax elements to extract raw, unmapped and unaligned reads encoded as said method, parsing the master index table to retrieve the encoded clusters signatures, decoding said clusters signatures by associating to each binary representation of the signature the corresponding sequence of nucleotides, parsing the vector of integers associated to each signature to retrieve on a storage medium the Access Units containing the coded representation of the genomic data, extracting multiple blocks of syntax elements from the Access Units by employing header information.

In another aspect said decoding method further comprises decoding a genomic dataset header containing global configuration parameters, In another aspect said decoding method further comprises decoding a master index table containing coded clusters signatures and coded blocks offsets, In another aspect of said decoding method said genomic reads are paired In another aspect of said decoding method said genomic reads are entropy decoded A genomic encoder (1115) for the compression of raw, unmapped and unaligned genome sequence data (111), said genome sequence data (111) comprising reads of sequences of nucleotides, said genomic encoder (1115) comprising:

a clustering unit (112), configured to partition said reads in group of reads that share a common sequence or subsequence of nucleotides called cluster signatures thereby creating clusters of reads (113) and clusters signatures (114), one or more descriptors encoding units (115), configured to encode said clustered reads as blocks of syntax elements.

one or more entropy encoding units (1110), configured to compress said blocks of syntax elements according to their statistical properties to produce Genomic Access Units (1111)

a signatures encoding unit (116) configured to binarize the clusters signatures (114) by associating a unique binary representation to each symbol of the clusters signatures.

a Genomic Dataset Header and Master Index Table generator (119) configured to associate said binarized cluster signatures (117) to a vector of integers expressing the offset on a storage medium of the entropy coded descriptors contained in the Genomic Access Units (1111)

a multiplexer (1113) for multiplexing the compressed genomic data and metadata

A genomic encoder (1210) for the compression of genome sequence data (121), said genome sequence data (121) comprising reads of sequences of nucleotides, said genomic encoder (1210) comprising:

an aligner unit (122), configured to align said reads to one or more reference sequences thereby creating aligned reads, a data classification unit (124), configured to classify said aligned reads according to specified matching rules with the one or more pre-existing reference sequences or constructed reference sequences thereby creating classes of aligned reads (128);

one or more descriptors encoding units (125-127), configured to encode said classified aligned reads as blocks of syntax elements by selecting said syntax elements according to said classes of aligned reads, one or more entropy encoding units (1212-1214), configured to compress said blocks of syntax elements according to their statistical properties to produce Genomic Streams (1215), a raw, unmapped and unaligned sequence reads encoding unit (1115) configured as described above, a multiplexer (1216) for multiplexing the compressed genomic data and metadata.

A genomic encoder comprising coding means capable of executing said encoding methods comprising that said clusters signatures are encoded by associating each nucleotide of the supported alphabet to a unique binary representation, and that said binary representations of each nucleotide are concatenated in a signature to obtain a bitstring representing the encoded signature.

A genomic decoder (1313) for the decompression of a compressed genomic Access Units (134) said genomic decoder (1313) comprising:

a demultiplexer (132) for demultiplexing compressed genomic Access Units (134) and Genomic Dataset Header and Master Index Table (133)

parsing means (135) configured to parse said Genomic Dataset Header and Master Index Table (133) into encoded clusters signatures (137), a signatures decoder (139) configured to decode said encoded clusters signatures (137) into clusters signatures (1311), entropy decoders (136) configured to decompress said compressed genomic Access Units into blocks of syntax elements named Genomic Descriptors (138), one or more descriptors decoders (1310), configured to decode the genomic descriptors into uncompressed reads of sequences of nucleotides (1312), A genomic decoder (148) for the decompression of a compressed genomic stream (1410) said genomic decoder (148) comprising:

a demultiplexer (140) for demultiplexing compressed genomic data and metadata into genomic bitstreams (141) and bitstreams of unmapped sequence reads (145)

entropy decoders (142-144) configured to parse said compressed genomic stream into blocks of syntax elements named genomic descriptors (145), one or more genomic descriptors decoders (146-147), configured to decode the genomic descriptors into classified reads of sequences of nucleotides (1411), genomic data classes decoders (149) configured to selectively decode said classified reads of sequences of nucleotides on one or more reference sequences so as to produce uncompressed reads of sequences of nucleotides, an unmapped sequence reads decoder (1313) configured as described above to produce uncompressed raw, unmapped and unaligned sequence reads (1414) and clusters signatures (1415).

The present invention further provides a computer-readable medium comprising instructions that when executed cause at least one processor to perform all the aspects of the previously mentioned encoding methods.

The present invention further provides a computer-readable medium comprising instructions that when executed cause at least one processor to perform all the aspects of the previously mentioned coding methods.

The present invention further provides a computer-readable medium comprising instructions that when executed cause at least one processor to perform all the aspects of the previously mentioned decoding methods.

The present invention further provides a support data storing genomic encoded according perform all the aspects of the previously mentioned coding methods.

DETAILED DESCRIPTION

The genomic or proteomic sequences referred to in this invention include, for example, and not as a limitation, nucleotide sequences, Deoxyribonucleic acid (DNA) sequences, Ribonucleic acid (RNA), and amino acid sequences. Although the description herein is in considerable detail with respect to genomic information in the form of a nucleotide sequence, it will be understood that the methods and systems for compression can be implemented for other genomic or proteomic sequences as well, albeit with a few variations, as will be understood by a person skilled in the art.

Genome sequencing information is generated by High Throughput Sequencing (HTS) machines in the form of sequences of nucleotides (a. k. a. "bases") represented by strings of letters from a defined vocabulary. The smallest vocabulary is represented by five symbols: {A, C, G, T, N} representing the 4 types of nucleotides present in DNA namely Adenine, Cytosine, Guanine, and Thymine. In RNA Thymine is replaced by Uracil (U). N indicates that the sequencing machine was not able to call any base and so the real nature of the nucleotide at that position is undetermined. In case the IUPAC ambiguity codes are adopted by the sequencing machine as vocabulary, the alphabet used for the symbols is composed of the following symbols: {A, C, G, T, U, W, S, M, K, R, Y, B, D, H, V, N or -}. In case of amino acids the supported symbols are: {A, C, D, E, F, G, H, I, K, L, M, N, P, Q, R, S, T, V, W, Y}.

In the context of the present invention a Genomic Dataset is defined as any structured set of genomic data including, for example, genomic data of a living organism, one or more sequences and metadata generated by the genomic sequencing of a living organism or by any other step of genomic data processing performed on the original sequencing data.

In the context of the present invention a Genomic Dataset Header is defined as a data structure containing global parameters used by the encoding and decoding devices processing data coded according to this invention disclosure.

The nucleotides sequences produced by sequencing machines are called reads. Sequence reads can be composed of a number of nucleotides ranging between a few dozens to several thousand. Some sequencing technologies produce sequence reads composed of pairs of which one read is originated from one DNA strand and the other is originated from the other strand. A read associated to another read in a sequencing process producing pairs is said to be its mate.

Throughout this disclosure, a reference sequence is a sequence of nucleotides associated to a mono-dimensional integer coordinate system for which each integer coordinate is associated to a single nucleotide. Coordinate values can only be equal or larger than zero. This coordinate system in the context of this invention is zero-based (i.e. the first nucleotide has coordinate 0 and it is said to be at position 0) and linearly increasing from left to right.

Figure 3:
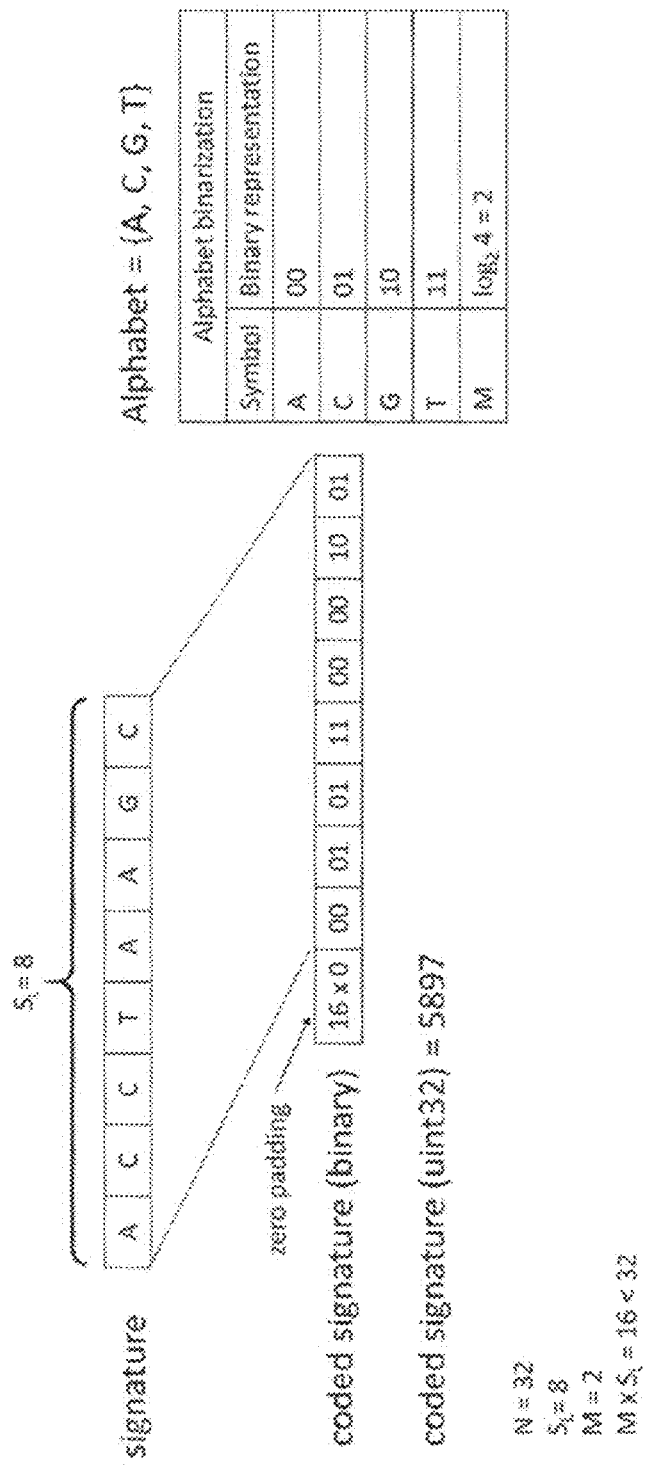
FIG. 3 shows how to encode a signature of length 8 as an unsigned 32-bit integer in case of constant length signature.

When mapping sequence reads on a reference sequence, said reference sequence is used as axis of a mono-dimensional coordinate system in which the left-most position is denoted as position 0. In a sequence read, mapped to a reference sequence, the nucleotide composing the read mapped at the reference sequence position identified by the smallest coordinate number is usually referred to as the "left-most" nucleotide, whereas the nucleotide composing the read mapped at the reference sequence position identified by the largest coordinate number is referred to as the "right-most" nucleotide. This is illustrated in FIG. 3. Throughout this disclosure, a nucleotide is also referred to as a base.

When a sequence read is mapped to a reference sequence, the coordinate of the left-most mapped base is said to represent the mapping position of the read on the reference sequence.

A base present in the aligned read and not present in the reference sequence (a.k.a. insertion) and bases preserved by the alignment process but not mapped on the reference sequence (a.k.a. soft clips) do not have mapping positions.

When a sequence read cannot be mapped to any mapped position of the used reference sequences according to the specified matching rules, it is said to be unmapped.

The process of building longer genomic sequences by looking for overlapping regions among sequence reads is called assembly.

A longer genomic sequence built assembling shorter reads is called contig.

Sequence reads that fail to build any contig during an assembly process are said to be unaligned.

Throughout this invention disclosure the process of grouping reads according to some shared characteristic is defined clustering. The groups of reads sharing the same characteristic are called clusters. A schematic of this concept is provided in FIG. 1.

Figure 2:
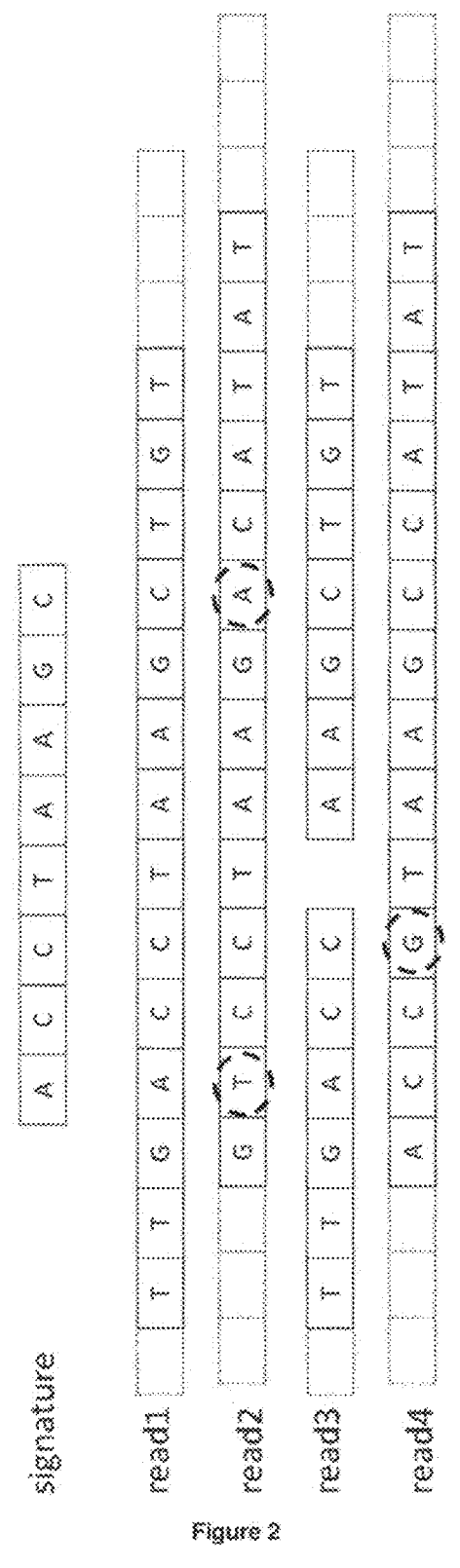

Throughout this invention disclosure the characteristic shared among sequence reads belonging to the same cluster is called cluster signature or signature. Examples of reads containing a signature with different degrees of accuracy are provided in FIG. 2. A signature can be composed by any number of nucleotides from two to several thousands and signatures can have either constant length for all clusters or variable length. The alphabet of symbols that can belong to a signature depends on the specific genomic sample that has been sequenced to produce the sequence reads being processed. As an example, but not as a limitation, the following alphabets can be used:

for DNA
{A, G, C, T, N}
{A, G, C, T, R, Y, S, W, K, M, B, D, H, V, N, ., -}
(IUPAC notation)

for RNA
{A, G, C, U, N}
{A, G, C, U, R, Y, S, W, K, M, B, D, H, V, N, ., -}
(IUPAC notation)

for amino acids
{A, C, D, E, F, G, H, I, K, L, M, N, P, Q, R, S, T, V, W, Y}

The type of alphabet used to compute a cluster signature is identified by a parameter Alphabet_ID carried by a data structure called Genomic Dataset Header described in this disclosure.

Signatures of clusters belonging to the same genomic dataset can be of constant or variable length. A global parameter encoded in the genomic dataset header is used to signal if the signatures length is constant or variable. If the signature length is constant a second global parameter represents the length in symbols of the clusters signatures. This value is 0 in case of variable signatures length.

A reference genome is composed by one or more reference sequences and it is assembled by scientists as a representative example of a species' set of genes. For example GRCh37, the Genome Reference Consortium human genome (build 37) is derived from thirteen anonymous volunteers from Buffalo, N.Y. However, a reference sequence could also consist of a synthetic sequence conceived and merely constructed to improve the compressibility of the reads in view of their further processing.

The read composing a read pair with a base mapping on the smallest coordinate on a reference is referred to, in this disclosure, as "Read 1" whereas its mate is referred to as "Read 2".

The distance, expressed as number of nucleotides (or bases), separating two reads generated as a pair, by a sequencing machine using today technology, is unknown, and it is determined by mapping both reads composing the pair (i.e. minimizing appropriate matching functions) to a reference sequence.

As detailed in the following sections, this invention disclosure defines a method to classify sequence reads according to the result of their mapping on one or more reference sequences:

Reads which map on a reference sequence without and mismatch belong to Class P

Reads which map on a reference sequence with only unknown bases (represented by the symbol "N") as mismatches belong to Class N Reads which map on a reference sequence with a number of substitutions with respect to the reference below a defined threshold belong to Class M Reads which map on a reference sequence with a number of substitutions, deletions, insertions or soft clipped bases with respect to the reference below a defined threshold belong to Class I Read pair with one mapped read (belonging to any of the previous four classes) and an unmapped mate belong to Class HM Read which do not map on any reference sequence according to established constraints in terms of maximum number of allowed mismatches belong to Class U An Access Unit (AU) is defined as a logical data structure containing a coded representation of genomic information or related metadata to facilitate the bit stream access and manipulation. It is the smallest data organization that can be decoded by a decoding device implementing the invention described in this disclosure.

An Access Unit can contain reads belonging to only one data class defined in this disclosure.

According to the type of coded information, an AU can be decoded either independently of any other AU or using information contained in other AUs.

Unmapped or unaligned reads belonging to Class U are encoded using a specific sub-set of syntax elements stored in Access Units of a specific type.

An example of Access Unit is illustrated in FIG. 10. Access Units are composed by blocks of encoded descriptors (described in the next section). To enable transport over a network, blocks are further decomposed into packets.

Descriptors are syntax elements representing part of the information necessary to reconstruct (i.e. decode) coded reference sequences, sequence reads and the associated mapping information. Different types of descriptors are defined to express:

- the mapping position of a read on a reference sequence,
- the distance between a read and its mate,
- the length of a sequence read,
- the position of mismatches in aligned reads with respect to reference sequences,
- the types of mismatches with respect to reference sequences at the associated positions,
- the bases that could not be mapped on the reference sequence by the mapping procedure and are classified as "soft clipped" bases,
- the sequence reads lengths,
- the mapping flags as specified by the SAM specification,
- the multiple mapping positions that are associated to a single read or read pair by the mapping procedure,
- the identification of the existence of spliced reads (i.e. reads that when split in chunks find mapping positions with higher degrees of matching accuracy then when they are mapped as single connected read mapped on a single position on a reference sequence)
- the specific type of reference sequence used such as:
  - reference genomes as those published by consortia like the Genome Reference Consortium (e.g. GRCh37), the University of California Santa Cruz (e.g. hg19),
  - reference sequences built by using specified sets of reads and specified sets of assembly rules,
- the positions and types of modifications applied to reference sequences with the objective of reducing the entropy of the descriptors used to represent the mismatches of sequence reads mapped on such modified reference sequences,
- the representation of sequence reads that cannot be mapped at any position of the reference sequence with specified degrees of matching accuracy,
- the representation of sequence reads that cannot be aligned to build any contig during an assembly process according to specified degrees of matching accuracy,
- the representation of entire reference sequences or portions thereof.

According to the method disclosed in this invention, reference sequences or portion thereof, sequence reads and the associated alignment information are coded using a sub-set of the descriptors listed above which are then entropy coded using a multiplicity of entropy coders according to each descriptor specific statistical properties. Blocks of descriptors with homogeneous statistical properties are structured in Access Units which represent the smallest coded representation of one or more genomic sequence that can be manipulated by a device implementing the invention described in this disclosure.

The invention described in this disclosure defines a method to index Access Units containing the coded representation of raw sequence reads, unmapped sequence reads and unaligned sequence reads.

Classification of the Sequence Reads According to Matching Rules

The sequence reads generated by sequencing machines are classified by the disclosed invention into six different "classes" according to the matching results of the alignment with respect to one or more "pre-existing" reference sequences.

When aligning a DNA sequence of nucleotides with respect to a reference sequence the following cases can be identified:

1. A region in the reference sequence is found to match the sequence read without any error (i.e. perfect mapping). Such sequence of nucleotides is referenced to as "perfectly matching read" or denoted as "Class P".
2. A region in the reference sequence is found to match the sequence read with a type and a number of mismatches determined only by the number of positions in which the sequencing machine generating the read was not able to call any base (or nucleotide). Such type of mismatches are denoted by an "N", the letter used to indicate an undefined nucleotide base. In this document this type of mismatch are referred to as "n type" mismatch. Such sequences belong to "Class N" reads. Once the read is classified to belong to "Class N" it is useful to limit the degree of matching inaccuracy to a given upper bound and set a boundary between what is considered a valid matching and what it is not. Therefore, the reads assigned to Class N are also constrained by setting a threshold (MAXN) that defines the maximum number of undefined bases (i.e. bases called as "N") that a read can contain. Such classification implicitly defines the required minimum matching accuracy (or maximum degree of mismatch) that all reads belonging to Class N share when referred to the corresponding reference sequence, which constitutes an useful criterion for applying selective data searches to the compressed data.
3. A region in the reference sequence is found to match the sequence read with types and number of mismatches determined by the number of positions in which the sequencing machine generating the read was not able to call any nucleotide base, if present (i.e. "n type" mismatches), plus the number of mismatches in which a different base, than the one present in the reference, has been called. Such type of mismatch denoted as "substitution" is also called Single Nucleotide Variation (SNV) or Single Nucleotide Polymorphism (SNP). In this document this type of mismatch is also referred to as "s type" mismatch. The sequence read is then referenced to as "M mismatching reads" and assigned to "Class M". Like in the case of "Class N", also for all reads belonging to "Class M" it is useful to limit the degree of matching inaccuracy to a given upper bound, and set a boundary between what is considered a valid matching and what it is not. Therefore, the reads assigned to Class M are also constrained by defining a set of thresholds, one for the number "n" of mismatches of "n type" (MAXN) if present, and another for the number of substitutions "s" (MAXS). A third constraint is a threshold defined by any function of both numbers "n" and "s", f(n,s). Such third constraint enables to generate classes with an upper bound of matching inaccuracy according to any meaningful selective access criterion. For instance, and not as a limitation, f(n,s) can be (n+s)1/2 or (n+s) or any linear or non-linear expression that sets a boundary to the maximum matching inaccuracy level that is admitted for a read belonging to "Class M". Such boundary constitutes a very useful criterion for applying the desired selective data searches to the compressed data when analyzing sequence reads for various purposes because it makes possible to set a further boundary to any possible combination of the number of "n type" mismatches and "s type" mismatches (substitutions) beyond the simple threshold applied to the one type or to the other.

4. A fourth class is constituted by sequencing reads presenting at least one mismatch of any type among "insertion", "deletion" (a.k.a. indels) and "clipped", plus, if present, any mismatches type belonging to class N or M. Such sequences are referred to as "I mismatching reads" and assigned to "Class I". Insertions are constituted by an additional sequence of one or more nucleotides not present in the reference, but present in the read sequence. In this document this type of mismatch is referred to as "i type" mismatch. In literature when the inserted sequence is at the edges of the sequence it is also referred to as "soft clipped" (i.e. the nucleotides are not matching the reference but are kept in the aligned reads contrarily to "hard clipped" nucleotides which are discarded). In this document this type of mismatch is referred to as "c type" mismatch. Keeping or discarding nucleotides is a decisions taken by the aligner stage and not by the classifier of reads disclosed in this invention which receives and processes the reads as they are determined by the sequencing machine or by the following alignment stage. Deletion are "holes" (missing nucleotides) in the read with respect to the reference. In this document this type of mismatch is referred to as "d type" mismatch. Like in the case of classes "N" and "M" it is possible and appropriate to define a limit to the matching inaccuracy. The definition of the set of constraints for "Class I" is based on the same principles used for "Class M" and is reported in Table 1 in the last table lines. Beside a threshold for each type of mismatch admissible for Class I data, a further constraint is defined by a threshold determined by any function of the number of the mismatches "n", "s", "d", "i" and "c", w(n,s,d,i,c). Such additional constraint make possible to generate classes with an upper bound of matching inaccuracy according to any meaningful user defined selective access criterion. For instance, and not as a limitation, w(n,s,d,i,c) can be (n+s+d+i+c)1/5 or (n+s+d+i+c) or any linear or non-linear expression that sets a boundary to the maximum matching inaccuracy level that is admitted for a read belonging to "Class I". Such boundary constitutes a very useful criterion for applying the desired selective data searches to the compressed data when analyzing sequence reads for various purposes because it enables to set a further boundary to any possible combination of the number of mismatches admissible in "Class I" reads beyond the simple threshold applied to each type of admissible mismatch.

5. A fifth class includes all reads that do not find any mapping considered valid (i.e not satisfying the set of matching rules defining an upper bound to the maximum matching inaccuracy as specified in Table 1) for each data class when referring to the reference sequence. Such sequences are said to be "Unmapped" when referring to the reference sequences and are classified as belonging to the "Class U".

Classification of Read Pairs According to Matching Rules

The classification specified in the previous section concerns single sequence reads. In the case of sequencing technologies that generates read in pairs (i.e. Illumina Inc.) in which two reads are known to be separated by an unknown sequence of variable length, it is appropriate to consider the classification of the entire pair to a single data class. A read that is coupled with another is said to be its "mate".

If both paired reads belong to the same class the assignment to a class of the entire pair is obvious: the entire pair is assigned to the same class for any class (i.e. P, N, M, I, U). In the case the two reads belong to a different class, but none of them belongs to the "Class U", then the entire pair is assigned to the class with the highest priority defined according to the following expression:

$$P<N<M<I$$

in which "Class P" has the lowest priority and "Class I" has the highest priority.

In case only one of the reads belongs to "Class U" and its mate to any of the Classes P, N, M, I a sixth class is defined as "Class HM" which stands for "Half Mapped".

Figure 15:
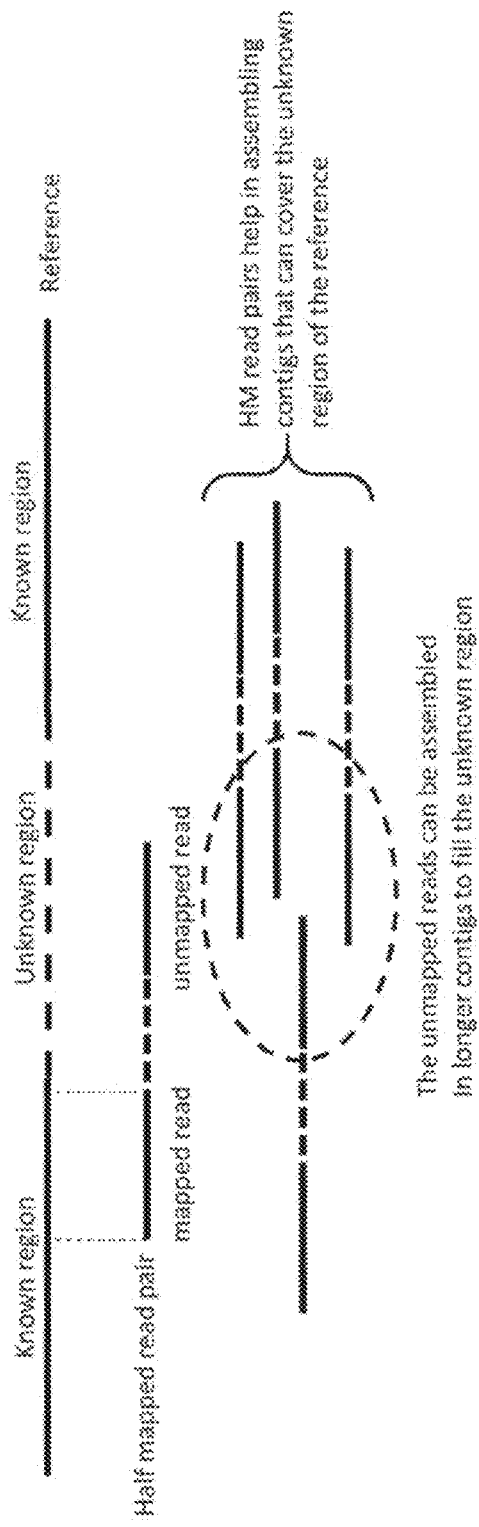
FIG. 15 shows how half mapped read pairs (Class HM) can be used to fill unknown regions of a reference sequence by assembling longer sequences ("also known as "contigs"") with unmapped reads.

The definition of such specific class of reads is motivated by the fact that it is used for attempting to determine gaps or unknown regions existing in reference genomes (a.k.a. little known or unknown regions). Such regions are reconstructed by mapping pairs at the edges using the pair read that can be mapped on the known regions. The unmapped mate is then used to build the so called "contigs" of the unknown region as it is shown in FIG. 15. Therefore providing a selective access to only such type of read pairs greatly reduces the associated computation burden enabling much efficient processing of such data originated by large amounts of data sets that using the state of the art solutions would require to be entirely inspected.

The table below summarizes the matching rules applied to reads in order to define the class of data each read belongs to. The rules are defined in the first five columns of the table in terms of presence or absence of type of mismatches (n, s, d, i and c type mismatches). The sixth column provide rules in terms of maximum threshold for each mismatch type and any function f(n,s) and w(n,s,d,i,c) of the possible mismatch types.

TABLE 1

Type of mismatches and set of constrains that each sequence reads must satisfy
to be classified in the data classes defined in this invention disclosure.

Number and types of mismatches found when matching a read with
a reference sequence

| Number of unknown bases ("N") | Number of substitutions | Number of deletions | Number of Insertions | Number of clipped bases | Set of matching accuracy constraints | Assignement Class |
|---|---|---|---|---|---|---|
| 0 | 0 | 0 | 0 | 0 | 0 | P |
| n > 0 | 0 | 0 | 0 | 0 | n ≤ MAXN | N |
|  |  |  |  |  | n > MAXN | U |
| n ≥ 0 | s > 0 | 0 | 0 | 0 | n ≤ MAXN and s ≤ MAXS and f(n, s) ≤ MAXM | M |
|  |  |  |  |  | n > MAXN or s > MAXS or f(n, s) > MAXM | U |
| n ≥ 0 | s ≥ 0 | d ≥ 0* | i ≥ 0* | c ≥ 0* | n ≤ MAXN and s ≤ MAXS and d ≤ MAXD and i ≤ MAXI and c ≤ MAXC w(n, s, d, i, c) ≤ MAXTOT | I |
|  |  | *At least one mismatch of type d, i, c must be present (i.e. d > 0 or i > 0 or c > 0) |  |  |  |  |
|  |  | d ≥ 0 | i ≥ 0 | c ≥ 0 | n > MAXN or s > MAXS or d > MAXD or i > MAXI or c > MAXC w(n, s, d, i, c) > MAXTOT | U |

Compressed Representation of Genomic Sequence Reads and Reference Sequences

A common element of efficient approaches to genomic sequence reads compression is the exploitation of the correlation of sequence data with respect to a reference sequence. Even if the somatic profile of the human population is extremely diversified, the actual portion of the number of nucleotides that differs from person to person is about only 0.1% of the total number of nucleotides composing an entire genome. Therefore, the specific genomic information characterizing each individual is very limited with respect to the entire information carried by an entire genome. When a pre-existing reference genome is available, be it for previous sequencing or as a published "average" consensus reference, the most efficient way to encode the actual information is to identify and encode only the differences with respect to the reference genome.

In order to do so with raw sequence reads in the form of FASTQ data, a preliminary pre-processing step of mapping on an available reference genome is performed. In case a reference genome is not available or if the bias introduced by the usage of a specific reference is not desirable, the construction of a new reference sequence by means of assembling the available sequence reads into longer sequences is a possible alternative.

When sequence reads have been mapped with respect to a pre-existing or to a constructed reference sequence, each sequence read can be fully represented by a number of elements denoted in this disclosure as "read descriptors" or simply "descriptors".

For example, in the case of a sequence read that perfectly matches a segment of a reference sequence, the only sub-set of descriptors needed to represent the sequence read is composed by the coordinate of the mapping position on the reference (usually the coordinate of the mapping position of the left-most base of the sequence read), the length of the sequence read itself and the information indicating if the read is mapping on the direct or reverse DNA strand with respect to the reference sequence strand.

In case it is not possible to find any mapping position for which all the bases of the sequence read match all bases of the reference sequence, the mapping (or mappings) with the minimal number of mismatches are retained. In such case a different sub-set of descriptors is needed to also express the substitutions, the insertions, the deletions and the clipped bases that may occur in correspondence of the mapping position with the minimal or close to minimal number of mismatches. With such sub-set of descriptors the sequence reads can be reconstructed using the information carried by the descriptors and the information carried by the reference sequence.

The mapping process can also produce other types of information such as: multiple possible mapping positions and related scores, the quality of mapping, the specification of spliced reads, the mapping on two different references (usually chromosomes) of reads belonging to a pair, features of the sequencing process (e.g. PCR or optical duplicate). All such information requires specific additional descriptors that extend each sub-sets that then is compressed by applying for each sub-set of descriptors appropriate entropy coding algorithms.

The genome sequencing process can generate read duplicates (i.e. two or more exact copies of the same genomic sequence) due to:
- the chemistry of the genome sequencing process (Polymerase Chain Reaction duplicate),
- the data acquisition process (optical duplicate). A read is called as an optical duplicate if the pair of reads are both on the same tile, and the distance between reads is less than a given configuration parameter depending on the experiment.

Each read or read pair can therefore be uniquely represented by a specific sub-set of descriptors according to the results of the mapping process.

Commonly used approaches such as SAM and CRAM do not encode reads or read pairs according to the specific sub-set of descriptors needed to represent their mapping information. SAM and CRAM do not classify sequence reads into data classes according to the number and type of mismatches they contain with respect to the reference sequence they are mapped to. Furthermore, these formats do not code sequence reads separately into Access Units containing in compressed form only sequence reads belonging to a single data class. In the case of sequence reads generated in pairs, state of the art approaches do not code them as single elements partitioned into classes according to their mapping accuracy with respect to the reference sequence. Such state of the art approaches are characterized by the following limitations and drawbacks:

1. The coding of reads or reads pairs without classifying sequence reads into separate data classes according to mapping results versus a reference sequence and using a unique super-set of descriptors is an inefficient approach that yields poor compression performance.
2. The coding of read pairs as separate sequence reads requires the duplication of several descriptors carrying the same information, thus results inefficient and yields poor compression performance.
3. The retrieval of the information needed to reconstruct read pairs result to be complex and inefficient since the process requires a brute-force sequential search in possibly the entire dataset which as in case of next generation sequencing (NGS) technology can be extremely large.
4. The selective access to read or read pairs mapped to specific genomic regions requires to search the entire dataset to have the guarantee that all reads or read pairs are retrieved.

When coding read pairs by means of a single sub-set of descriptors, the following technical advantages are evident to a person skilled in the art:

1. The information common to both reads, which is clearly redundant, is not replicated by coding a pair as single element (e.g. read pair identifiers, mapping distance, mapping reference identifiers, the various mapping quality information currently encoded by specific flags in the SAM file format)
2. The retrieval of the mutual pairing information (i.e. the information providing which read is the mate of any read at hand) is straightforward and does not require any further processing. Conversely in the state of the art approaches it may require to parse the entire volume of data.

In order to enable efficient selective access to specific portions of sequencing data and being able to transport them on a digital data network, the set of descriptors used to represent sequence reads aligned to a reference are structured in logically separate and independent data blocks called Access Units (AU). Each Access Unit contains only the compressed representation of a single data class, and can be decoded either independently of any other Access Units or using only Access Units carrying the coded representation of the reference sequence region used for mapping. This enables selective access and out-of-order transport capabilities.

In order to increase the compression efficiency this invention eliminates the need of specifying the "mapping reference identifier" descriptor for each read pair having both pairs mapped on the same reference sequence. Each Access Unit can contain only reads or pairs that map on the same reference. Using such solution the descriptor representing the reference sequence identifier needs to be encoded only once per each Access Unit or set of Access Units (and not repeated for each read as currently done in SAM/BAM formats).

The only exception of the rule expressed above is the case of read pairs having the two reads mapped on different reference sequences (e.g. chromosomes). In this case the pair is split and the two reads are coded as two separate genomic records and each encoded read contains the identifier of the reference sequence its mate is mapped to.

A person skilled in the art knows that classifying information in groups of elements with homogeneous statistical properties provides better compression performance with respect to the usage of a general purpose compressor (e.g. LZ type algorithm) applied to a heterogeneous set of data. As a consequence, when encoding genomic sequence reads in pairs by means of a specific sub-set of descriptors, higher compression is achieved thanks to the lower entropy characterizing each separate sub-set of descriptors and higher processing efficiency when reconstructing and retrieving read pairs.

Clustering Genomic Sequence Reads

The invention described in this disclosure comprises the step of creating groups—or "clusters"—of reads sharing a common sub-sequence of nucleotides (the signature) within given matching constraints. Reads belonging to a given cluster either contain the exact and complete signature or have a number of mismatches (substitutions, insertions or deletions) below a defined threshold. An example of reads sharing a signature with different degrees of accuracy is provided in FIG. 2. Example of thresholds include:

the total number of mismatches of any type,
a total score obtained by assigning a different weight to each mismatch type and then summing up the weights of all mismatches in each read,
a weighted sum of the occurrences of substitutions, insertions, deletions and clipped bases.

Each cluster of reads described above is coded in one or more Access Units. Each Access Unit is therefore associated to one cluster signature.

Throughout this invention disclosure the cluster signature associated to a cluster coded into an Access Unit is also referred to as "Access Unit signature".

For coding reasons, two or more Access Units can share the same signature in case e.g. a limit is set on the maximum number of reads coded per AU; that is, a Cluster may be coded with more than one Access Unit.

Encoding Signatures

According to this invention disclosure, once all genomic sequences have been included in a cluster, signatures are encoded as sequences of one or more N bits integers. The signature is encoded as one or more N bits integers according to the following steps:

According to the specific clustering algorithm adopted, the clusters signatures can be of variable or constant length. If the length is constant, a global parameter signaling the constant signature length is set accordingly and the length is stored in the genomic dataset header. Otherwise the global parameter signaling the variable signature length is set accordingly and the length is set to 0 in the genomic dataset header.

Each symbol of the supported alphabet is uniquely associated to a binary representation of length equal to M=ceil(log₂(cardinality of the supported alphabet)) in case of constant signature length M=ceil(log₂(cardinality of the supported alphabet)+1) in case of variable signature length Here ceil is the operation returning the least integer that is greater than or equal to its argument.

In case of variable signatures length, one sequence of bits is reserved to represent a special symbol called terminator used to signal the end of a coded signature.

Figure 4:
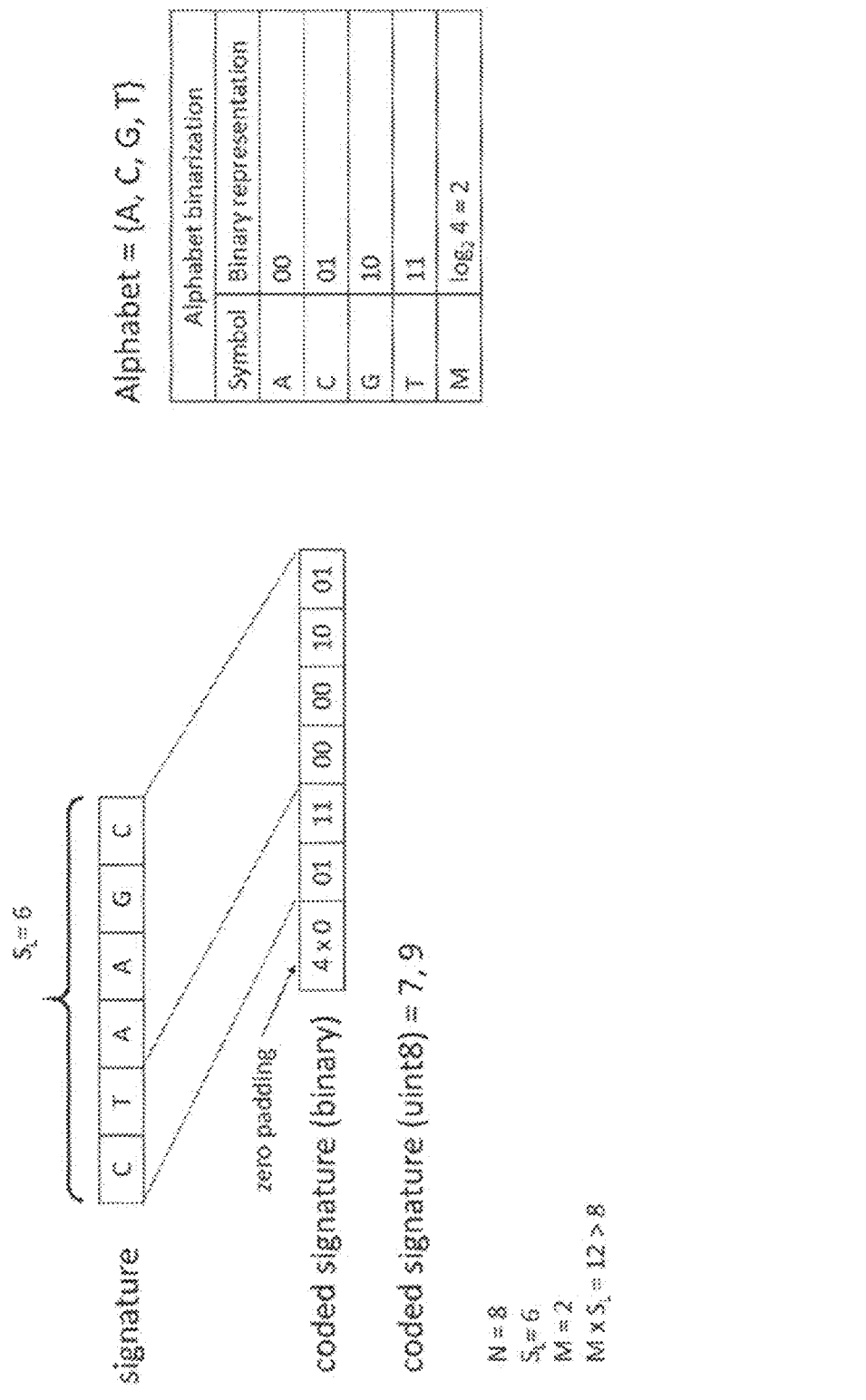
FIG. 4 shows how to encode a signature of length 6 as several unsigned 8-bit integers in case of constant length signature.

In case of constant signatures length, which in this disclosure is referred to as $S_L$ if $M \times S_L <= N$ the binary representations of contiguous symbols in the signature are concatenated in a single bitstring possibly padding with 0 the Most Significant Bits if $M \times S_L < N$. An example is provided in FIG. 3 for N=32 and a four symbols alphabet.

if $M \times S_L > N$ the binary representations of contiguous symbols in the signature are concatenated in two or more bitstring possibly padding with 0 the Most Significant Bits of each bitstrings if $b_s$ is not an exact divisor (also known as aliquot part) of N. An example is provided in FIG. 4 for N=8 and a four symbols alphabet.

Figure 5:
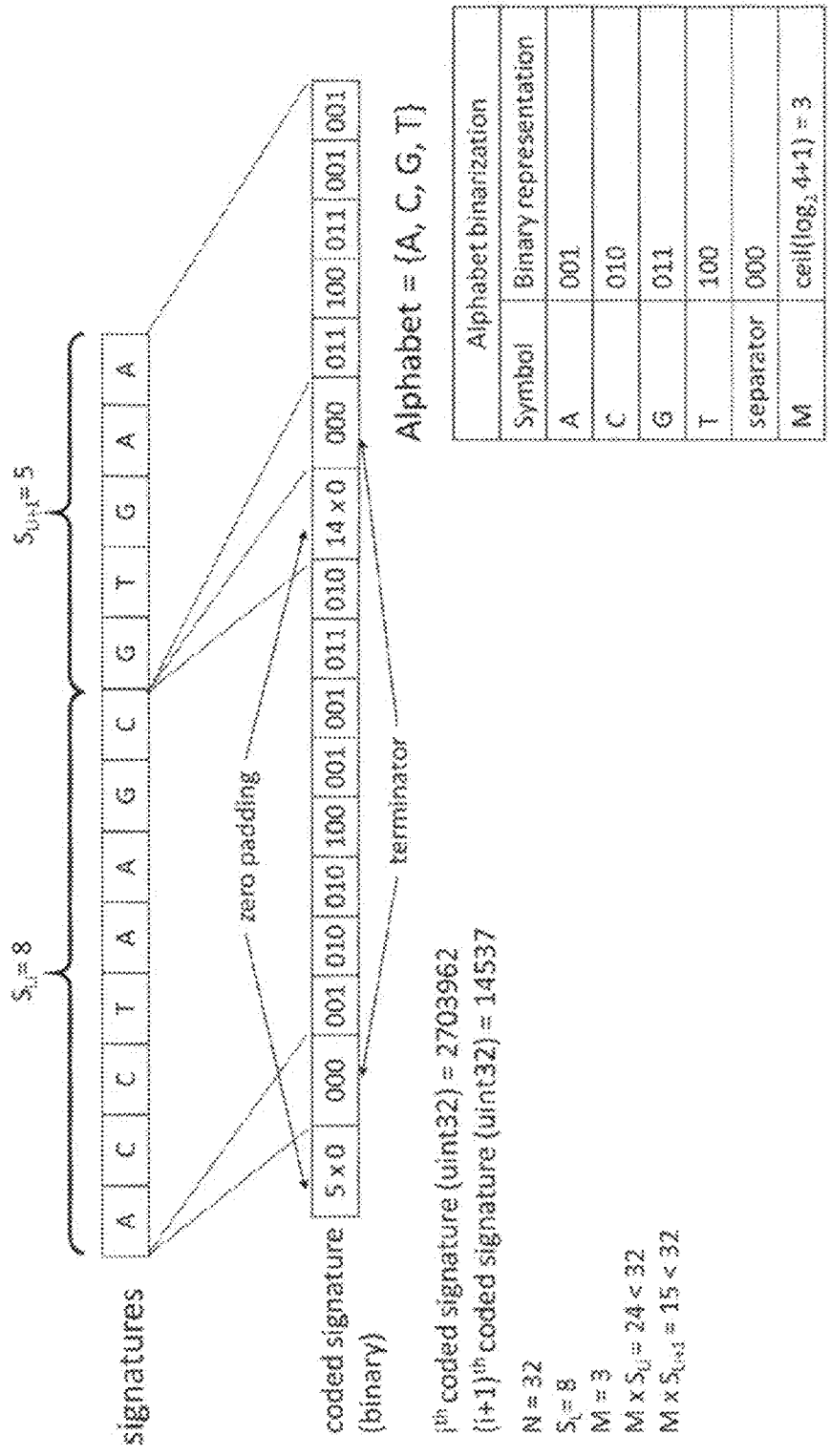
FIG. 5 shows how to encode signatures of length 8 and 5 as an unsigned 32-bit integers in case of variable length signatures.
Figure 6:
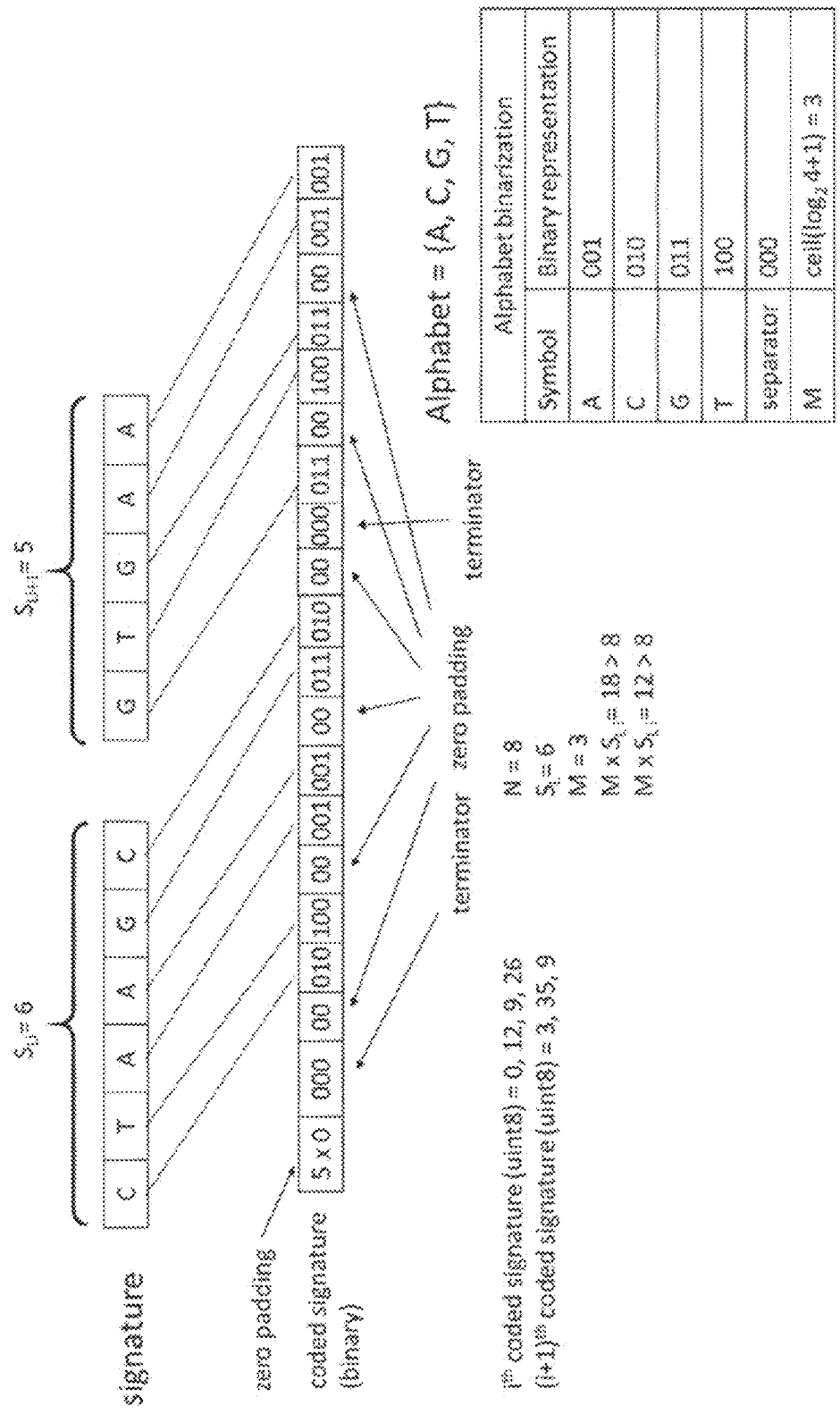
FIG. 6 shows how to encode signatures of length 6 and 5 as several unsigned 8-bit integers in case of variable length signatures.

In case of variable signatures length, which in this disclosure is referred to as $S_{Li}$ for the $i^{th}$ signature if $M \times S_{Li} <= N$ the binary representations of contiguous symbols in the signature are concatenated in a single bitstring. After all coded symbols have been concatenated the bitstring is terminated with a terminator symbol added at the Most Significant Bits position and if necessary the remaining Most Significant Bits are padded with 0. An example is provided in FIG. 5 for N=32 and a four symbols alphabet.

if $M \times S_{Li} > N$ the binary representations of contiguous symbols in the signature are concatenated in two or more bitstring possibly padding with 0 the Most Significant Bits of each bitstrings if $b_s$ is not an exact divisor (also known as aliquot part) of N. The last bitstring is terminated by the terminator symbol and further padded with 0 at the Most Significant Bits positions. An example is provided in FIG. 6 for N=8 and a four symbols alphabet.

Indexing Compressed Genomic Data for Efficient Selective Access

In order to support selective access to specific regions of the aligned data, this invention disclosure defines two data structures: a Genomic Dataset Header carrying global parameters and the indexing tool called Master Index Table (MIT) used during the encoding and decoding process. The syntax of the Genomic Dataset Header is provided in Table 2 and the syntax of the Master index table is provided in Table 3. This invention disclosure defines how to support raw, unmapped and unaligned reads indexing with elements comprised in the MIT and the Genomic Dataset Header.

Genomic Dataset Header

The Genome Dataset Header is a data structure carrying global parameters used by the encoder and the decoder to manipulate the encoded genomic information. The components and meaning of each element of the Genomic Dataset Header are listed in Table 2 below.

Global parameters related to the indexing mechanism disclosed in this invention are coded in the Genomic Dataset Header as reported in Table 2. These include:

the number of bits used to represent each integer value of the encoded signatures. This is represented by U_signature_size in Table 2;

the number of clusters and associated signatures the raw, unmapped and unaligned reads have been partitioned into. This is represented by U_clusters_num in Table 2;

a flag indicating if the signatures have a constant or variable length in terms of nucleotides. This is represented by U_signature_constant_length in Table 2;

the signature length in case of constant signatures length. This is represented by U_signature_length in Table 2.

TABLE 2

| Syntax | Semantic |
|---|---|
| Genomic Dataset Header syntax. | |
| Dataset_Header { | |
| Dataset_Group_ID | Identifier of Dataset Group ID |
| Dataset_ID | Identifier of the Dataset. Its value shall be one of the IDs listed in the Datasets Group Header. |
| Major_Brand | Brand identifier, identifying the data (compression) format specification the Dataset complies with. |
| Minor_Version | Minor version number of the data (compression) format specification the Dataset complies with. |
| Reads_Length | Length of reads in nucleotides. 0 in case of variable reads length. |
| Paired_Reads | 1 if all reads in the Dataset are paired, 0 otherwise. |
| Block_Header_Flag | If set, all Blocks composing the Dataset are preceded by a Block Header |
| CC_Mode_Flag | Used to signal the AU coding mode: AUC/CC or AUC/GRC. If set, two Access Units of one class cannot be separated by Access Units of a different class in the storage device. If unset, Access Units are ordered by Access Unit Start Position in the storage device. |
| Alphabet_ID | A unique identifier for the type of alphabet used to encode mismatches of sequence reads with respect to the reference sequences. For example it is used to signal if DNA, RNA, IUPAC alphabets are used. |

TABLE 2-continued

Genomic Dataset Header syntax.

| Syntax | Semantic |
|---|---|
| Seq_Count | Number of reference sequences used in this Dataset. |
| for (seq=0; seq<Seq_Count; seq++) { | |
| Reference_ID[seq] | Unique identification number of the reference within this Dataset Group. |
| Sequence_ID[seq] | Unambiguous identifier identifying the reference sequence(s) used in this Dataset. In common reference genomes such as GRCh37 these include at least the 24 chromosomes identifiers. |
| } | |
| for (seq=0;seq<Seq_Count;seq++) { | |
| Seq_Blocks[seq] | Number of AUs per sequence. A value of 0 means not specified (e.g. in Transport Format). |
| } | |
| Dataset type | Type of genomic data coded in the dataset. For example "aligned", "not aligned". |
| Num_Classes | Number of classes encoded in the Dataset. |
| for (Class_ID =0;Class_ID<Num_Classes; Class_ID ++) { | |
| Num_Descriptors[Class_ID] | Maximum number of Descriptors per Class encoded in the Dataset. |
| } | |
| U_clusters_num | Number of clusters of unmapped reads |
| U_signature_constant_length | 1 = constant length<br>0 = variable length |
| U_signature_size | Size in bits of the encoded signatures |
| if(U_signature_constant_length){ | |
| U_signature_length | Length of clusters signature in nucleotides |
| } | |
| } | |

Master Index Table

An indexing tool called Master Index Table (MIT) is disclosed in this invention.

The Master Index Table (MIT) is a data structure based on multi-dimensional array containing:

The position, as number of nucleotides, of the left-most matching base among the primary alignments of all reads or read pairs contained in the Access Unit, as a set of Blocks from different Descriptors Streams, with regards to the reference sequence. This is represented by Start_AU_Ref_Position[Sequence_ID][Class_ID][AU_ID] in Table 3.

The position, as number of nucleotides, of the right-most matching base among the primary alignments of all reads or read pairs contained in the Access Unit, as a set of Blocks from different Descriptors Streams, with regards to the reference sequence. This is represented by End_AU_Ref_Position[Sequence_ID][Class_ID][AU_ID] in Table 3.

The byte offset of the first byte of each coded Block of descriptors composing each AU of each class encoded with respect to each reference sequence. The offset is calculated with respect to the first byte of the Dataset Payload (0-based). If the Block is empty and (1) Block_Header_Flag is set, it is equal to 0xFFFFFFFF. If the Block is empty and (2) Block_Header_Flag is unset, it is equal either to the Block_Byte_Offset value of the next block in the Descriptor Stream or, for the last Block in the Descriptor Stream, to the Descriptor Stream payload size. This is represented by Block_Byte_Offset[Sequence_ID][Class_ID][AU_ID][Descriptor_ID] in Table 3.

According to the coding method used, which is signaled by a global configuration parameter, two alternative blocks of information:

The size of each Access Unit in bytes if each Access Unit is stored on the storage medium as a contiguous block of data, or The size of each block of encoded descriptors if all descriptors of the same type are encoded and stored on the storage medium as a contiguous block of data.

The last section of the MIT contains two alternative sections that are used according to the presence of headers prepended to each coded Block of descriptors. If Block headers are present (Block_Header_Flag set) the MIT contains the size in byte of each Descriptor Stream. If Block headers are not present (Block_Header_Flag unset) the MIT contains the size in bytes of each Access Unit.

The alternative between the two coding methods is signaled by the flag called Block_Header_Flag in Table 3.

TABLE 3

Master Index Table.

| Syntax | Semantics |
|---|---|
| Master_Index_Table { | |
| for (Sequence_ID=0;Sequence_ID<Seq_Count;Sequence_ID++) { | Sequence_ID is a unique identifier of a reference sequence and corresponds to the variable seq in |

TABLE 3-continued

Master Index Table.

| Syntax | Semantics |
|---|---|
| | the Dataset Header, as defined in Table 2.<br>Seq_Count is the total number of reference sequences and is encoded in the Dataset Header, as defined in Table 2. |
|     for (Class_ID=0;Class_ID<Num_Classes;Class_ID++) { | Num_Classes is equal to field Num_Classes of Dataset Header, as defined in Table 2. |
|         for (AU_ID=0;AU_ID<Seq_Blocks[Sequence_ID];AU_ID++) { | AU_ID is a unique identifier of the Access Unit.<br>Seq_Blocks is an array of number of blocks per reference sequence and is encoded in the Dataset Header, as defined in Table 2. |
|             Start_AU_Ref_Position[Sequence_ID][Class_ID][AU_ID] | The absolute position on the reference sequence identified by Sequence ID of the left-most mapped base among the primary alignments of all reads or read pairs contained in the AU and belonging to the class identified by Class_ID, in Access Unit identified by AU_ID. A reserved value is used if the Access Unit is empty. |
|             End_AU_Ref_Position[Sequence_ID][Class_ID][AU_ID] | The absolute position on the reference sequence identified by Sequence ID of the right-most mapped base among the primary alignments of all reads or read pairs contained in the AU and belonging to the class identified by Class_ID, in Access Unit identified by AU_ID. A reserved value is used if the Access Unit is empty. |
|             for (Descriptor_ID=0; Descriptor_ID < Num_Descriptors[Sequence_ID][Class_ID]; Descriptor_ID++) { | Num_Descriptors[Class_ID][Sequence_ID] is encoded in the Num_Descriptors field of the Dataset Header. Syntax of Num_Descriptors Dataset Header field is defined in Table 2. |
|                 Block_Byte_Offset[Sequence_ID][Class_ID][AU_ID][Descriptor_ID] | Byte offset of the first byte in the Block, with respect to the first byte of the Dataset Payload (0-based). If the Block is empty and (1) Block_Header_Flag is set it is equal to the reserved value signaling empty AU. If the Block is empty and (2) Block_Header_Flag is unset, it is equal either to the Block_Byte_Offset value of the next block in the Descriptor Stream or, for the last Block in the Descriptor Stream, to Descriptor_Stream_Size[Class_ID]. |
|             }<br>        }<br>    }<br>}<br>if (!Block_Header_Flag) { | Block_Header_Flag is encoded in the Dataset Header, as defined in Table 2. |
|     for (Class_ID=0;Class_ID<Num_Classes;Class_ID++) {<br>        for (Descriptor_ID=0; Descriptor_ID < Num_Descriptors[Seq_Count-1][Class_ID]; Descriptor_ID++) { | |
|             Descriptor_Stream_Size[Class_ID][Descriptor_ID] | Descriptors Stream size in bytes. |
|         }<br>    }<br>}<br>else {<br>    for (Sequence_ID=0;Sequence_ID<Seq_Count;Sequence_ID++) {<br>        for (Class_ID=0;Class_ID<Num_Classes;Class_ID++) {<br>            for (AU_ID=0;AU_ID< Seq_Blocks[Sequence_ID];AU_ID++) { | |
|                 AU_Size[Sequence_ID][Class_ID][AU_ID] | Access Unit size in bytes. |
|             }<br>        } | |

TABLE 3-continued

Master Index Table.

| Syntax | Semantics |
|---|---|
| `    }`<br>`  }`<br>`  for (Cluster_ID=0;Cluster_ID<U_Clusters_num;Cluster_ID++) {`<br>`    for (AU_ID=0;AU_ID<Seq_Blocks[Sequence_ID];AU_ID++) {`<br>`      U_Cluster_Signature[Cluster_ID][AU_ID]`<br>`      for (Descriptor_ID=0; Descriptor_ID <`<br>`Num_Descriptors[Sequence_ID][Class_ID]; Descriptor_ID++) {` | Cluster signature |
| `        U_Cluster_Byte_Offset[Cluster_ID][AU_ID][Descriptor_ID]` | Byte offset of the first byte in the Block, with respect to the first byte of the Dataset Payload (0-based). |
| `      }`<br>`    }`<br>`  }`<br>`}` | |

Indexing Tool for Raw, Unmapped and Unaligned Reads

This invention disclosure describes the indexing mechanism for raw, unmapped and unaligned sequence reads (Class U) comprised in the Master Index Table reported in Table 3. Said indexing mechanism comprises:

signatures encoded as N bits integers as previously described. This is represented by U_Cluster[Cluster_ID][0] in Table 3.

pointers to the physical location on a storage medium of the encoded clusters of reads corresponding to each signature in the first vector. This is represented by U_Cluster[Cluster_ID][1] in Table 3.

These two vectors are part of the MIT illustrated in FIG. 7.

The advantage of this solution is evident to a person skilled in the art since it enables rapid pattern matching without the need to decode any encoded data (the Access Units). The granularity of the pattern matching can be tuned by modifying the length of the clusters signatures. Short signatures will generate larger clusters and will enable a coarse search for patterns, while longer signatures will generate a larger number of smaller cluster and a finer pattern search.

Decoding Clusters Signatures

When a decoding device has to decode a signature encoded as described in this invention disclosure, the following steps are required:

Read the global parameters in the Genomic Dataset Header related to the number of clusters of raw, unmapped and unaligned reads, U_clusters_num the flag indicating if all the clusters have signature with the same length in nucleotides, U_signature_constant_length the number of bit used per each integer representing the encoded signatures, U_signature_size in case of constant length, the length, in nucleotides of each signature, U_signature_length Each U_Cluster[Cluster_ID][0] element of the bi-dimensional vector in the Master Index Table named U_Cluster, with 0≤Cluster_ID<U_clusters_num, is decoded as a sequence of U_signature_size bits integers in case of constant signature length, the number of integers to be read is known as $$\text{ceil}\left(\frac{\text{U\_signature\_length} \times \text{ceil}(\log_2(\text{cardinality of alphabet}))}{\text{U\_signature\_size}}\right)$$

where the ceil function returns the least integer that is greater than or equal to its argument.

Decoding constant length signatures is illustrated in FIG. 8.

in case of variable signature length, the decoder shall detect the first integer containing the terminator symbol in its binary representation in order to stop reading integers for a given signature. An example is provided in FIG. 9.

Each U_Cluster[Cluster_ID][1] element of the bi-dimensional vector in the Master Index Table named U_Cluster, with 0≤Cluster_ID<U_clusters_num, contains a vector of unsigned integers representing the offsets in bytes of the first byte in the Access Unit of each block of descriptors encoding the sequence reads belonging to the cluster associated to the corresponding signature. Such offset is expressed with respect to the first byte of the Dataset Payload (0-based).

Encoding Apparatus

Figure 11:
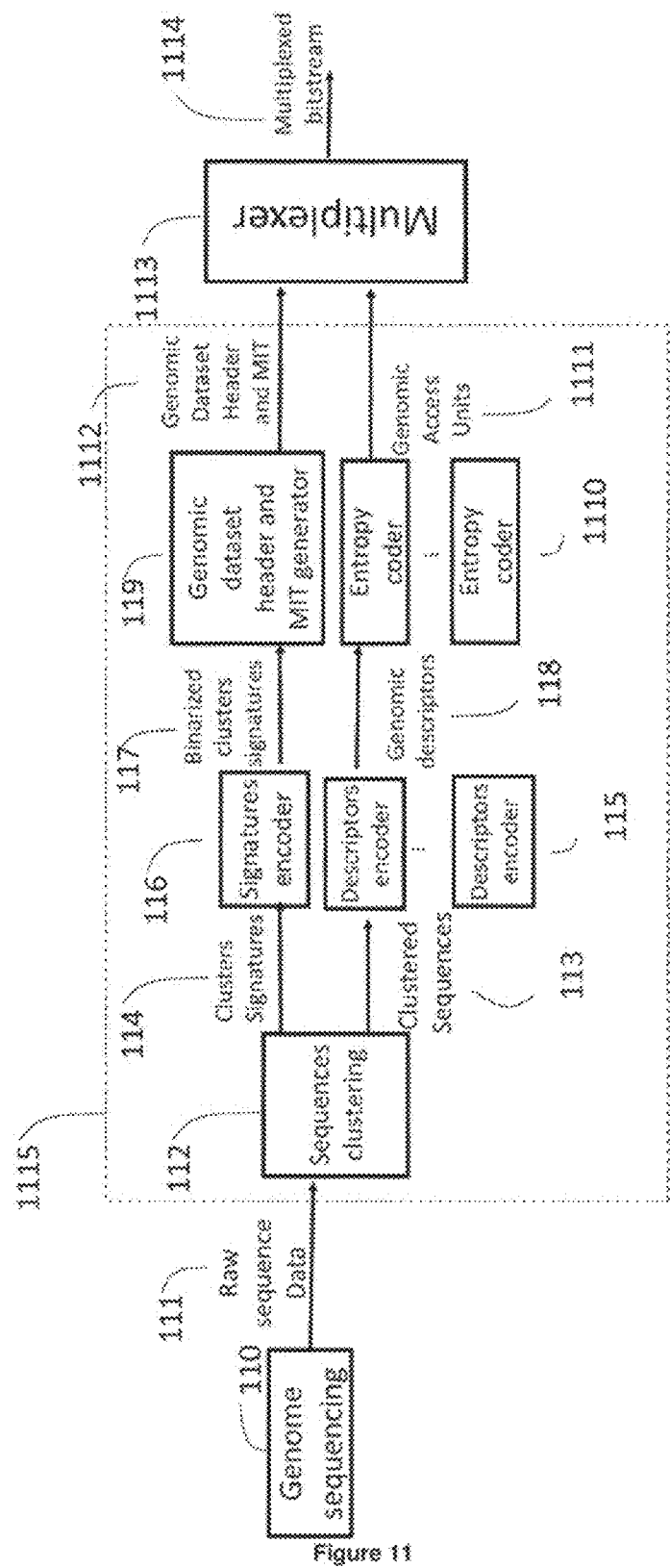
FIG. 11 shows the architecture of a raw genomic sequences encoder.

FIG. 11 shows an encoding apparatus 1115 according to the principles of this invention. The encoding apparatus 1115 receives as input a raw sequence data 111, for example produced by a genome sequencing apparatus 110. Genome sequencing apparatus 110 are known in the art, like the Illumina HiSeq 2500, the Thermo-Fisher Ion Torrent devices or the Oxford Nanopore MinION. The raw sequence data 111 is fed to a reads clustering unit 112, which prepares the sequences for encoding by clustering the reads that share a common sequence or subsequence of nucleotides called cluster signatures. The clustered sequence reads are then represented in terms of syntax elements named descriptors by descriptors encoder 115. The clusters signatures 114 generated by the clustering unit 112 are encoded by a signatures encoding unit 116. The genomic descriptors 118 generated by the descriptors encoder 115 are then entropy coded and structured as Genomic Access Units 1111. The binarized signatures 117 and global parameters the Genomic Dataset Header and the Master Index Table 1112 generated by a Genomic Dataset Header and MIT generator 119. The Genomic Access Units 1111, the Genomic Dataset Header and the Master Index Table are then multiplexed in a Multiplexed bitstream 1114.

Figure 12:
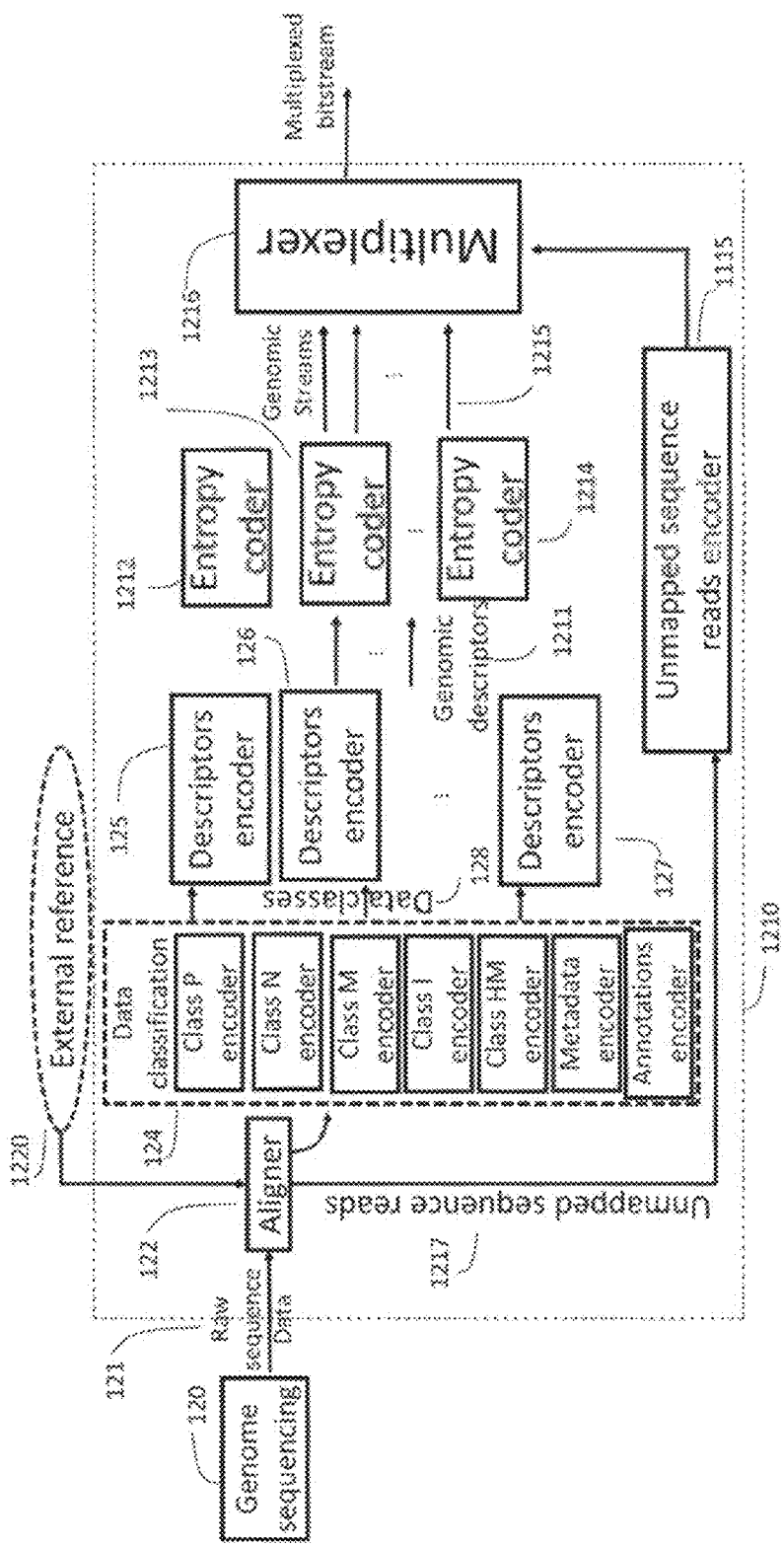
FIG. 12 shows the raw genomic sequences encoder of FIG. 11 integrated in a larger architecture encoding aligned reads as well.

The encoding apparatus 1115 can be part of a larger encoding apparatus 1210 shown in FIG. 12 where unmapped reads are encoded and multiplexed with encoded aligned reads. FIG. 12 shows an encoding apparatus 1210 according to the principles of this invention. The encoding apparatus 1210 receives as input a raw sequence data 121, for example produced by a genome sequencing apparatus 120. Genome sequencing apparatus 120 are known in the art, like the Illumina HiSeq 2500, the Thermo-Fisher Ion Torrent devices or the Oxford Nanopore MinION. The raw sequence data 121 is fed to an aligner unit 122, which prepares the sequences for encoding by aligning the reads to a reference sequence 1220. Sequence reads that cannot be aligned by the alignment unit 122 are classified as unmapped sequence reads (Class U data) 1217 and fed to an unmapped sequence reads encoder 1115. The internal architecture and inner working of the unmapped sequence reads encoder 1115 has been described in the previous paragraphs and it is shown in FIG. 11. The aligned sequences produced by the aligning unit 122 are then classified by data classification module 124. The data classes 128 are then fed to descriptors encoders 125-127. The genomic descriptors streams 1211 are then fed to arithmetic encoders 1212-1214 which encode the descriptors according to the statistical properties of the data or metadata carried by the descriptor streams. The result are one or more genomic streams 1215 multiplexed in a single bitstream by the multiplexing unit 1216.

Decoding Apparatus

Figure 13:
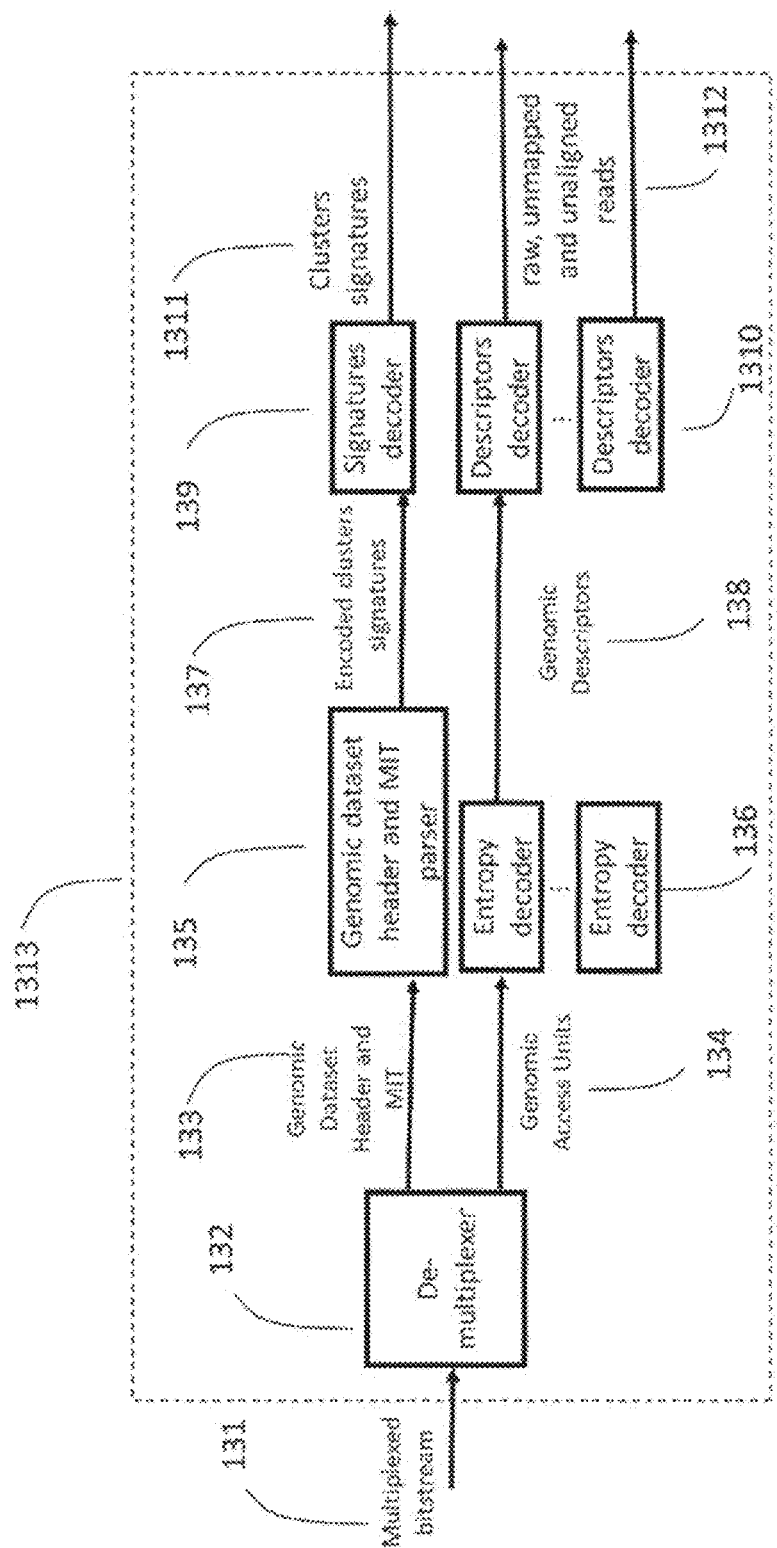
FIG. 13 shows the architecture of a decoder of Access Units containing raw, unmapped and unaligned sequence data. The output consists of clusters of decoded sequence reads and the associated signatures.

FIG. 13 shows a decoding apparatus 1313 according to the principles of this disclosure. A demultiplexing unit 132 receives a multiplexed bitstream 131 from a network or a storage element and extracts a Genomic Dataset Header and a Master Index Table 133 and Genomic Access Units 134. A decoding apparatus 1313 receives the Genomic Dataset Header and a Master Index Table 133 and Genomic Access Units 134 which are then fed respectively to a Genomic dataset header and MIT parser 135 and an entropy decoder 136. The encoded clusters signatures 137 extracted by the Genomic dataset and MIT parser 135 are then decoded by a signatures decoder 139 to produce Cluster signatures 1311. The genomic descriptors streams 138 are fed to descriptors decoder 1310 to further decode the descriptors into raw, unmapped and unaligned sequence reads 1312.

Figure 14:
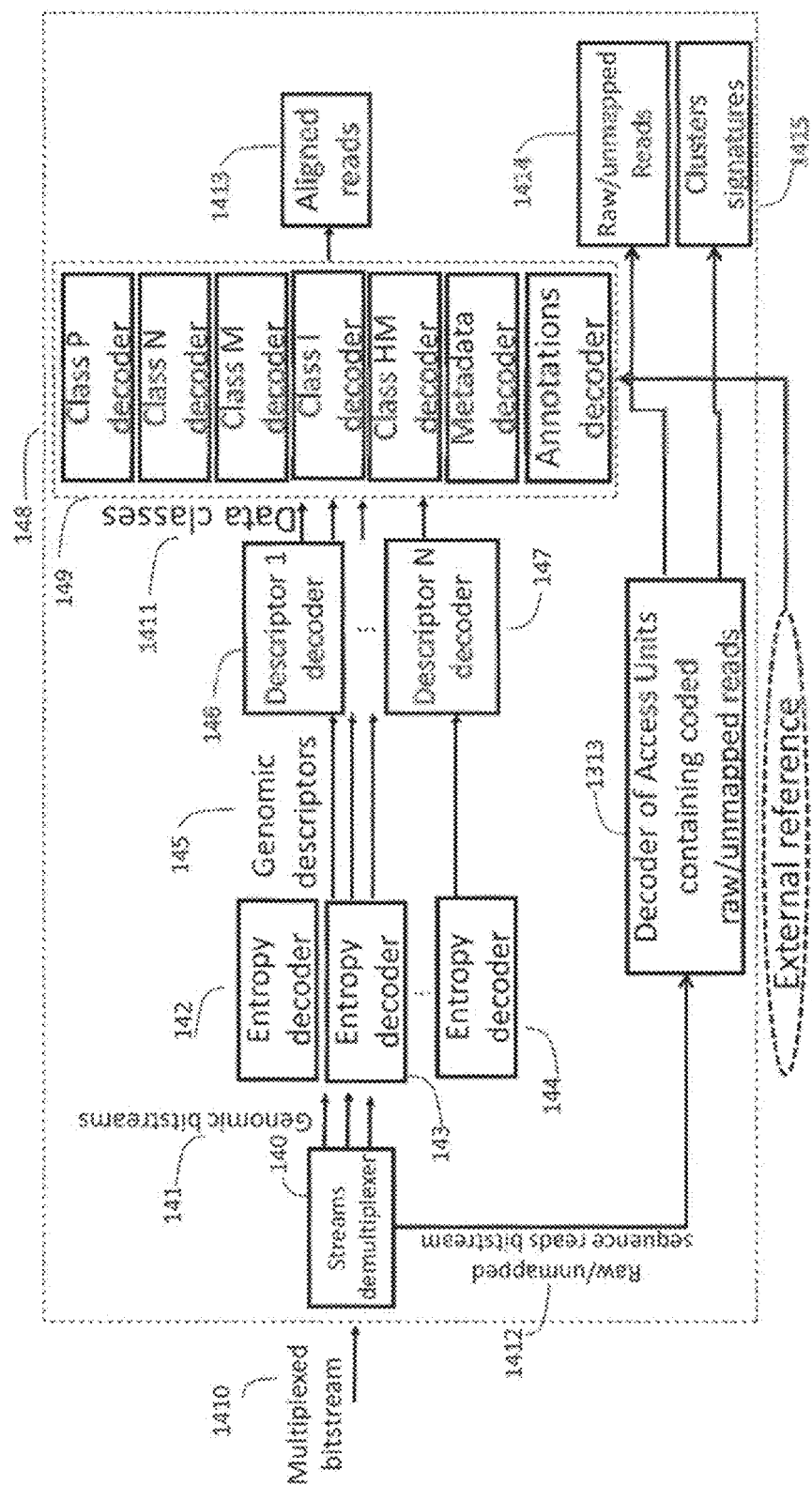
FIG. 14 shows the decoder of FIG. 12 used in a genomic sequences decoder to decode Access Units containing unmapped reads (Class U data).

FIG. 14 shows how the Class U decoder described above and shown in FIG. 13 can be part of a larger decoder of genomic sequence reads. FIG. 14 shows a decoding apparatus 148 according to the principles of this disclosure. A Stream Demultiplexer 140 receives a multiplexed genomic bitstream 1410 from a network or a storage element to produce separate genomic bitstreams 141 which are then fed to entropy decoders 142-144, to produce genomic descriptors streams 145.

Bitstreams containing Access Units encoding raw, unmapped and unaligned sequence reads (Class U) 1412 are fed to a decoder of Access Units containing raw, unmapped and unaligned sequence reads 1313 described above and shown in FIG. 13. The extracted genomic descriptors streams 145 are fed to descriptors decoders 146-147 to further decode the descriptors into classes of genomic data. Class decoders 149 further process the genomic descriptors 1411 and merge the results to produce uncompressed aligned sequence reads.

Class decoders 149 are able to reconstruct the original genomic sequences by leveraging the information on the original reference sequences carried by one or more genomic. In case the reference sequences are not transported by the genomic streams they must be available at the decoding side and accessible by the class decoders.

The inventive techniques herewith disclosed may be implemented in hardware, software, firmware or any combination thereof. When implemented in software, these may be stored on a computer medium and executed by a hardware processing unit. The hardware processing unit may comprise one or more processors, digital signal processors, general purpose microprocessors, application specific integrated circuits or other discrete logic circuitry.

The techniques of this disclosure may be implemented in a variety of devices or apparatuses, including mobile phones, desktop computers, servers, tablets and similar devices.

The invention claimed is:

1. A method for encoding genome sequence data, said genome sequence data comprising reads of sequences of nucleotides, wherein said reads are classified according to their mapping on reference sequences and wherein reads unmapped on said reference sequences are encoded using a specific subset of syntax elements as follows:
   partitioning said unmapped reads into clusters of reads which share a common sequence or subsequence of nucleotides called cluster signature, wherein reads belong to a cluster if they either contain the exact and complete signature or have a number of mismatches below a defined threshold,
   encoding said clustered reads as a multiplicity of blocks of syntax elements, and
   structuring said blocks of syntax elements with header information thereby creating successive Access Units.

2. The method of claim 1, wherein said clusters signatures are encoded by:
   associating each nucleotide of the supported alphabet to a unique binary representation, and
   concatenating said binary representations of each nucleotide in a signature to obtain a bitstring representing the encoded signature.

3. The method of claim 2, wherein each cluster of encoded sequence reads is identified by said encoded signature.

4. The method of claim 3, wherein said blocks of syntax elements are associated with a master index table, comprising cluster signatures encoded and associated to a vector of integer values representing the positions on a storage medium of the blocks of encoded syntax elements representing the sequence reads belonging to each cluster.

5. The method of claim 4, wherein said blocks of syntax elements are associated with a genomic dataset header comprising one or more of:
   a dataset group identifier used to uniquely identify each dataset group,
   a genomic dataset identifier used to uniquely identify each dataset,
   a brand identifier used to identify the data format specification the dataset complies with,
   a minor version number used to identify the data format specification the dataset complies with,
   the length of encoded genomic reads in nucleotides used to signal constant length reads,
   a flag signaling the presence of paired end reads,
   a flag signaling the presence of blocks headers,
   a flag signaling the order in which Access Units are stored on a storage medium in order to facilitate data access when decoding said Access Units,
   the number of reference sequences used to code the dataset,
   a numeric identifier per each reference sequence used to uniquely identify each reference sequence,
   a string identifier per each reference sequence used to uniquely identify each reference sequence,
   the number of coded Access Units per reference sequence used to count the Access Units associated to each reference sequence, the type of coded genomic data used to distinguish among aligned reads, unaligned reads, unmapped reads and reference sequences, the number of data classes coded in the dataset, the number of descriptors used per each data class coded in the dataset used during the decoding process, the total number of clusters used to index encoded unmapped reads, the number of bits used to represent the integer values used to encode the cluster signatures used to decode encoded clusters signatures, a flag signaling if all the cluster signatures have the same length in terms of number of nucleotides, and the length of the clusters signatures.

6. The method of claim 5, wherein said genomic reads are paired.

7. The method of claim 6, wherein said genomic data are entropy coded.

8. A non-transitory computer-readable medium comprising instructions that when executed cause at least one processor to perform the encoding method of claim 1.

9. A genomic encoder for encoding genome sequence data, said genome sequence data comprising reads of sequences of nucleotides, wherein said reads are classified according to their mapping on reference sequences and wherein said reads include reads unmapped on said reference sequences, said genomic encoder comprising:

a clustering unit, configured to partition said unmapped reads in clusters of reads that share a common sequence or subsequence of nucleotides called a cluster signature, wherein reads belong to a cluster if they either contain the exact and complete signature or have a number of mismatches below a defined threshold, one or more encoding units configured to encode said clustered reads into a multiplicity of blocks of syntax elements, one or more structuring units, configured to structure said blocks of syntax elements with header information thereby creating successive Access Units.

10. The genomic encoder of claim 9, comprising:

a signatures encoding unit configured to binarize the clusters signatures by associating a unique binary representation to each symbol of the clusters signatures, a Genomic Dataset Header and Master Index Table generator configured to associate said binarized cluster signatures to a vector of integers expressing the offset on a storage medium of the entropy coded descriptors contained in the Genomic Access Units, and a multiplexer for multiplexing the compressed genomic data and metadata.

11. The genomic encoder of claim 9, wherein said structuring units comprise entropy encoding units, configured to compress said blocks of syntax elements according to their statistical properties.

12. A genomic decoder for decoding encoded genomic data comprising:

a demultiplexer configured for receiving a bitstream of encoded genomic data and for providing as output Access Units, wherein the Access Units are representative of encoded genome sequence data, each Access Unit being classified in a type of a set of types based on the mapping of reads of sequences of nucleotides encoded in said Access Unit on reference sequences, wherein said Access Units include at least one Access Unit of a determined type, wherein in said at least one Access Unit of the determined type reads of sequences of nucleotides which do not map on said reference sequences are encoded, one or more entropy decoders configured to decode said at least one Access Units of the determined type into blocks of syntax elements, and one or more descriptors decoders, configured to extract, from said blocks of syntax elements, reads of sequences of nucleotides partitioned into clusters of reads which share a common sequence or subsequence of nucleotides called a cluster signature, wherein reads belong to a cluster if they either contain the exact and complete signature or have a number of mismatches below a defined threshold.

13. The genomic decoder of claim 12, wherein said demultiplexer further provides as output a Genomic Dataset Header and a Master Index Table, the genomic decoder comprises:

parsing means configured to parse said Genomic Dataset Header and Master Index Table into encoded clusters signatures, a signatures decoder configured to decode said encoded clusters signatures into clusters signatures.

14. The genomic decoder of claim 12, wherein said blocks of syntax elements are associated with a genomic dataset header comprising one or more of:

a dataset group identifier used to uniquely identify each dataset group, a genomic dataset identifier used to uniquely identify each dataset, a brand identifier used to identify the data format specification the dataset complies with, a minor version number used to identify the data format specification the dataset complies with, the length of encoded genomic reads in nucleotides used to signal constant length reads, a flag signaling the presence of paired end reads, a flag signaling the presence of blocks headers, a flag signaling the order in which Access Units are stored on a storage medium in order to facilitate data access when decoding said Access Units, the number of reference sequences used to code the dataset, a numeric identifier per each reference sequence used to uniquely identify each reference sequence, a string identifier per each reference sequence used to uniquely identify each reference sequence, the number of coded Access Units per reference sequence used to count the Access Units associated to each reference sequence, the type of coded genomic data used to distinguish among aligned reads, unaligned reads, unmapped reads and reference sequences, the number of data classes coded in the dataset, the number of descriptors used per each data class coded in the dataset used during the decoding process, the total number of clusters used to index encoded unmapped reads, the number of bits used to represent the integer values used to encode the cluster signatures used to decode encoded clusters signatures, a flag signaling if all the cluster signatures have the same length in terms of number of nucleotides, and the length of the clusters signatures.

15. A method for decoding encoded genomic data comprising the steps of:
- receiving a bitstream including Access Units representative of encoded genome sequence data, each Access Unit being classified in a type of a set of types based on the mapping of reads of sequences of nucleotides encoded in said Access Unit on reference sequences;
- identifying at least one Access Unit of a determined type, wherein in said at least one Access Unit of the determined type reads of sequences of nucleotides which do not map on said reference sequences are encoded;
- for said at least one Access Unit of the determined type, performing the following steps:
- extracting, from said at least one Access Unit of the determined type, blocks of syntax elements;
- extracting, from said blocks of syntax elements, reads of sequences of nucleotides partitioned into clusters of reads which share a common sequence or subsequence of nucleotides called a cluster signature, wherein reads belong to a cluster if they either contain the exact and complete signature or have a number of mismatches below a defined threshold.

16. The decoding method of claim 15, further comprising decoding a genomic dataset header containing global configuration parameters.

17. The decoding method of claim 16, further comprising decoding a master index table containing coded clusters signatures and coded blocks offsets.

18. The decoding method of claim 17, wherein said genomic reads are paired.

19. The decoding method of claim 18, wherein said genomic data are entropy decoded.

20. A non-transitory computer-readable medium comprising instructions that when executed cause at least one processor to perform the decoding method of claim 15.

21. The method of claim 15 wherein said bitstream further comprises a master index table, wherein extracting said blocks of syntax elements comprises:
- extracting the master index table from the bitstream;
- parsing the master index table to retrieve encoded clusters signatures;
- decoding the encoded clusters signatures by associating to a binary representation of each clusters signatures a corresponding sequence of nucleotides;
- parsing a vector of integers associated to each signature to retrieve on a storage medium said at least one Access Units of the determined type; and
- extracting said blocks of syntax elements from the retrieved at least one Access Unit of the determined type.

* * * * *

UNITED STATES PATENT AND TRADEMARK OFFICE
CERTIFICATE OF CORRECTION

| | |
|---|---|
| PATENT NO. | : 11,404,143 B2 |
| APPLICATION NO. | : 16/337642 |
| DATED | : August 2, 2022 |
| INVENTOR(S) | : Claudio Alberti et al. |

It is certified that error appears in the above-identified patent and that said Letters Patent is hereby corrected as shown below:

On the Title Page

Page 2
Item (30) Foreign Application Priority Data
Please delete "Feb. 14, 2017 (WO) ...................... PCT/US2017/01781" and replace with
-- Feb. 14, 2017 (WO) ...................... PCT/US2017/017841 --

Signed and Sealed this
Fifth Day of December, 2023

Katherine Kelly Vidal
*Director of the United States Patent and Trademark Office*